United States Patent [19]

Pan

[11] Patent Number: 5,989,909
[45] Date of Patent: Nov. 23, 1999

[54] HUCHORDIN AND USES THEREOF

[75] Inventor: Yang Pan, Brookline, Mass.

[73] Assignee: Millennium BioTherapeutics, Inc., Cambridge, Mass.

[21] Appl. No.: 08/938,365

[22] Filed: Sep. 26, 1997

[51] Int. Cl.$^6$ ............................ C12N 15/12; C12N 15/63; C12N 5/10
[52] U.S. Cl. ........................ 435/325; 536/23.5; 435/69.1; 435/320.1; 435/252.3; 530/350; 514/12
[58] Field of Search ................................. 435/69.1, 320.1, 435/325, 252.3; 514/12; 530/350; 536/23.5

[56] References Cited

U.S. PATENT DOCUMENTS

| | | | |
|---|---|---|---|
| 5,679,783 | 10/1997 | De Robertis et al. | 536/23.5 |
| 5,846,770 | 12/1998 | LaVallie | 435/69.1 |

FOREIGN PATENT DOCUMENTS

WO 96/29411  9/1996  WIPO.
WO 98/21335  5/1998  WIPO.

OTHER PUBLICATIONS

Piccolo et al., "Dorsoventral Patterning in Xenopus: Inhibition of Ventral Signals by Direct Binding of Chordin to BMP–4" Cell 86:589–598, 1996.
Sasai et al., "Xenopus chordin: A Novel Dorsalizing Factor Activated by Organizer–Specific Homeobox Genes" Cell 79:779–790, 1994.
Tolsma et al., "Peptides Derived from Two Separate Domains of the Matrix Protein Thrombospondin–1 Have Anti–Angiogenic Activity" J. of Cell. Biol. 122(2):497–511, 1993.
Volpert et al., "Inhibition of Angiogenesis by Thrombospondin–2" Biochem. & Biophys. Research Comm. 217(1):326–332, 1995.

*Primary Examiner*—Rebecca E. Prouty
*Attorney, Agent, or Firm*—Fish & Richardson, P.C.

[57] ABSTRACT

The invention relates to huchordin polypeptides, nucleic acid molecules encoding huchordin, and uses thereof.

19 Claims, 5 Drawing Sheets

```
  M    P    S    L    P    A    P    P    A    P    L    L    L    L    G    L    L    L    L    G     20
ATG  CCG  AGC  CTC  CCG  GCC  CCG  CCG  GCC  CCG  CTG  CTG  CTC  CTC  GGG  CTG  CTG  CTG  CTC  GGC     60

S    R    P    A    R    G    A    G    P    E    P    P    V    L    P    I    R    S    E    K     40
TCC  CGG  CCG  GCC  CGC  GGC  GCC  GGC  CCA  GAG  CCC  CCC  GTG  CTG  CCC  ATC  CGT  TCT  GAG  AAG    120

E    P    L    P    V    R    G    A    A    G    C    T    F    G    G    K    V    Y    A    L     60
GAG  CCG  CTG  CCC  GTT  CGG  GGA  GCG  GCA  GGC  TGC  ACC  TTC  GGC  GGG  AAG  GTC  TAT  GCC  TTG    180

D    E    T    W    H    P    D    L    G    E    P    F    G    V    M    R    C    V    L    C     80
GAC  GAG  ACG  TGG  CAC  CCG  GAC  CTA  GGG  GAG  CCA  TTC  GGG  GTG  ATG  CGC  TGC  GTG  CTG  TGC    240

A    C    E    A    P    Q    W    G    R    R    T    R    G    P    G    R    V    S    C    K    100
GCC  TGC  GAG  GCG  CCT  CAG  TGG  GGT  CGC  CGT  ACC  AGG  GGC  CCT  GGC  AGG  GTC  AGC  TGC  AAG    300

N    I    K    P    E    C    P    T    P    A    C    G    Q    P    R    Q    L    P    G    H    120
AAC  ATC  AAA  CCA  GAG  TGC  CCA  ACC  CCG  GCC  TGT  GGG  CAG  CCG  CGC  CAG  CTG  CCG  GGA  CAC    360

C    C    Q    T    C    P    Q    E    R    S    S    S    E    R    Q    P    S    G    L    S    140
TGC  TGC  CAG  ACC  TGC  CCC  CAG  GAG  CGC  AGC  AGT  TCG  GAG  CGG  CAG  CCG  AGC  GGC  CTG  TCC    420

F    E    Y    P    R    D    P    E    H    R    S    Y    S    D    R    G    E    P    G    A    160
TTC  GAG  TAT  CCG  CGG  GAC  CCG  GAG  CAT  CGC  AGT  TAT  AGC  GAC  CGC  GGG  GAG  CCA  GGC  GCT    480

E    E    R    A    R    G    D    G    H    T    D    F    V    A    L    L    T    G    P    R    180
GAG  GAG  CGG  GCC  CGT  GGT  GAC  GGC  CAC  ACG  GAC  TTC  GTG  GCG  CTG  CTG  ACA  GGG  CCG  AGG    540

S    Q    A    V    A    R    A    R    V    S    L    L    R    S    S    L    R    F    S    I    200
TCG  CAG  GCG  GTG  GCA  CGA  GCC  CGA  GTC  TCG  CTG  CTG  CGC  TCT  AGC  CTC  CGC  TTC  TCT  ATC    600

S    Y    R    R    L    D    R    P    T    R    I    R    F    S    D    S    N    G    S    V    220
TCC  TAC  AGG  CGG  CTG  GAC  CGC  CCT  ACC  AGG  ATC  CGC  TTC  TCA  GAC  TCC  AAT  GGC  AGT  GTC    660

L    F    E    H    P    A    A    P    T    Q    D    G    L    V    C    G    V    W    R    A    240
CTG  TTT  GAG  CAC  CCT  GCA  GCC  CCC  ACC  CAA  GAT  GGC  CTG  GTC  TGT  GGG  GTG  TGG  CGG  GCA    720

V    P    R    L    S    L    R    L    L    R    A    E    Q    L    H    V    A    L    V    T    260
GTG  CCT  CGG  TTG  TCT  CTG  CGG  CTC  CTT  AGG  GCA  GAA  CAG  CTG  CAT  GTG  GCA  CTT  GTG  ACA    780

L    T    H    P    S    G    E    V    W    G    P    L    I    R    H    R    A    L    A    A    280
CTC  ACT  CAC  CCT  TCA  GGG  GAG  GTC  TGG  GGG  CCT  CTC  ATC  CGG  CAC  CGG  GCC  CTG  GCT  GCA    840

E    T    F    S    A    I    L    T    L    E    G    P    P    Q    Q    G    V    G    G    I    300
GAG  ACC  TTC  AGT  GCC  ATC  CTG  ACT  CTA  GAA  GGC  CCC  CCA  CAG  CAG  GGC  GTA  GGG  GGC  ATC    900

T    L    L    T    L    S    D    T    E    D    S    L    H    F    L    L    L    F    R    G    320
ACC  CTG  CTC  ACT  CTC  AGT  GAC  ACA  GAG  GAC  TCC  TTG  CAT  TTT  TTG  CTG  CTC  TTC  CGA  GGG    960

L    L    E    P    R    S    G    G    L    T    Q    V    P    L    R    L    Q    I    L    H    340
CTG  CTG  GAA  CCC  AGG  AGT  GGG  GGA  CTA  ACC  CAG  GTT  CCC  TTG  AGG  CTC  CAG  ATT  CTA  CAC   1020

Q    G    Q    L    L    R    E    L    Q    A    N    V    S    A    Q    E    P    G    F    A    360
CAG  GGG  CAG  CTA  CTG  CGA  GAA  CTT  CAG  GCC  AAT  GTC  TCA  GCC  CAG  GAA  CCA  GGC  TTT  GCT   1080

E    V    L    P    N    L    T    V    Q    E    M    D    W    L    V    L    G    E    L    Q    380
GAG  GTG  CTG  CCC  AAC  CTG  ACA  GTC  CAG  GAG  ATG  GAC  TGG  CTG  GTG  CTG  GGG  GAG  CTG  CAG   1140
```

FIG. 1A

```
  M   A   L   E   W   A   G   R   P   G   L   R   I   S   G   H   I   A   A   R   400
ATG GCC CTG GAG TGG GCA GGC AGG CCA GGG CTG CGC ATC AGT GGA CAC ATT GCT GCC AGG  1200

K   S   C   D   V   L   Q   S   V   L   C   G   A   D   A   L   I   P   V   Q   420
AAG AGC TGC GAC GTC CTG CAA AGT GTC CTT TGT GGG GCT GAT GCC CTG ATC CCA GTC CAG  1260

T   G   A   A   G   S   A   S   L   T   L   L   G   N   G   S   L   I   Y   Q   440
ACG GGT GCT GCC GGC TCA GCC AGC CTC ACG CTG CTA GGA AAT GGC TCC CTG ATC TAT CAG  1320

V   Q   V   V   G   T   S   S   E   V   V   A   M   T   L   E   T   K   P   Q   460
GTG CAA GTG GTA GGG ACA AGC AGT GAG GTG GTG GCC ATG ACA CTG GAG ACC AAG CCT CAG  1380

R   R   D   Q   R   T   V   L   C   H   M   A   G   L   Q   P   G   G   H   T   480
CGG AGG GAT CAG CGC ACT GTC CTG TGC CAC ATG GCT GGA CTC CAG CCA GGA GGA CAC ACG  1440

A   V   G   I   C   P   G   L   G   A   R   G   A   H   M   L   L   Q   N   E   500
GCC GTG GGT ATC TGC CCT GGG CTG GGT GCC CGA GGG GCT CAT ATG CTG CTG CAG AAT GAG  1500

L   F   L   N   V   G   T   K   D   F   P   D   G   E   L   R   G   H   V   A   520
CTC TTC CTG AAC GTG GGC ACC AAG GAC TTC CCA GAC GGA GAG CTT CGG GGG CAC GTG GCT  1560

A   L   P   Y   C   G   H   S   A   R   H   D   T   L   S   V   P   L   A   G   540
GCC CTG CCC TAC TGT GGG CAT AGC GCC CGC CAT GAC ACG CTG TCC GTG CCC CTA GCA GGA  1620

A   L   V   L   P   P   V   K   S   Q   A   A   G   H   A   W   L   S   L   D   560
GCC CTG GTG CTA CCC CCT GTG AAG AGC CAA GCA GCA GGG CAC GCC TGG CTT TCC TTG GAT  1680

T   H   C   H   L   H   Y   E   V   L   L   A   G   L   G   G   S   E   Q   G   580
ACC CAC TGT CAC CTG CAC TAT GAA GTG CTG CTG GCT GGG CTT GGT GGC TCA GAA CAA GGC  1740

T   V   T   A   H   L   L   G   P   P   G   T   P   G   P   R   R   L   L   K   600
ACT GTC ACT GCC CAC CTC CTT GGG CCT CCT GGA ACG CCA GGG CTT CGG CGG CTG CTG AAG  1800

G   F   Y   G   S   E   A   Q   G   V   V   K   D   L   E   P   E   L   L   R   620
GGA TTC TAT GGC TCA GAG GCC CAG GGT GTG GTG AAG GAC CTG GAG CCG GAA CTG CTG CGG  1860

H   L   A   K   G   M   A   S   L   M   I   T   T   K   G   S   P   R   G   E   640
CAC CTG GCA AAA GGC ATG GCC TCC CTG ATG ATC ACC ACC AAG GGT AGC CCC AGA GGG GAG  1920

L   R   G   Q   R   R   T   V   I   C   D   P   V   V   C   P   P   P   S   C   660
CTC CGA GGG CAG AGA CGA ACG GTG ATC TGT GAC CCG GTG GTG TGC CCA CCG CCC AGC TGC  1980

P   H   P   V   Q   A   P   D   Q   C   C   P   V   C   P   E   K   Q   D   V   680
CCA CAC CCG GTG CAG GCT CCC GAC CAG TGC TGC CCT GTT TGC CCT GAG AAA CAA GAT GTC  2040

R   D   L   P   G   L   P   R   S   R   D   P   G   E   G   C   Y   F   D   G   700
AGA GAC TTG CCA GGG CTG CCA AGG AGC CGG GAC CCA GGA GAG GGC TGC TAT TTT GAT GGT  2100

D   R   S   W   R   A   A   G   T   R   W   H   P   V   V   P   P   F   G   L   720
GAC CGG AGC TGG CGG GCA GCG GGT ACG CGG TGG CAC CCC GTT GTG CCC CCC TTT GGC TTA  2160

I   K   C   A   V   C   T   C   K   G   G   T   G   E   V   H   C   E   K   V   740
ATT AAG TGT GCT GTC TGC ACC TGC AAG GGG GGC ACT GGA GAG GTG CAC TGT GAG AAG GTG  2220

Q   C   P   R   L   A   C   A   Q   P   V   R   V   N   P   T   D   C   C   K   760
CAG TGT CCC CGG CTG GCC TGT GCC CAG CCT GTG CGT GTC AAC CCC ACC GAC TGC TGC AAA  2280
```

FIG. 1B

```
   Q   C   P   V   G   S   G   A   H   P   Q   L   G   D   P   M   Q   A   D   G    780
  CAG TGT CCA GTG GGG TCG GGG GCC CAC CCC CAG CTG GGG GAC CCC ATG CAG GCT GAT GGG   2340

P   R   G   C   R   F   A   G   Q   W   F   P   E   S   Q   S   W   H   P   S    800
  CCC CGG GGC TGC CGT TTT GCT GGG CAG TGG TTC CCA GAG AGT CAG AGC TGG CAC CCC TCA   2400

V   P   P   F   G   E   M   S   C   I   T   C   R   C   G   A   G   V   P   H    820
  GTG CCC CCT TTT GGA GAG ATG AGC TGT ATC ACC TGC AGA TGT GGG GCA GGG GTG CCT CAC   2460

C   E   R   D   D   C   S   L   P   L   S   C   G   S   G   K   E   S   R   C    840
  TGT GAG CGG GAT GAC TGT TCA CTG CCA CTG TCC TGT GGC TCG GGG AAG GAG AGT CGA TGC   2520

C   S   R   C   T   A   H   R   R   P   A   P   E   T   R   T   D   P   E   L    860
  TGT TCC CGC TGC ACG GCC CAC CGG CGG CCA GCC CCA GAG ACC AGA ACT GAT CCA GAG CTG   2580

E   K   E   A   E   G   S   *
  GAG AAA GAA GCC GAA GGC TCT TAG                                                    868
                                                                                    2604

GGAGCAGCCAGAGGGCCAAGTGACCAAGAGGATGGGGCCTGAGCTGGGGAAGGGGTGGCATCGAGGACCTTCTTGCATT   2683

CTCCTGTGGGAAGCCCAGTGCCTTTGCTCCTCTGTCCTGCCTCTACTCCCACCCCCACTACCTTTGGGAACCACAGCTC   2762

CACAAGGGGGAGAGGCAGCTGGGCCAGACCGAGGTCACAGCCACTCCAAGTCCTGCCCTGCCACCCTCGGCCTCTGTCC   2841

TTGGAAGCCCCACCCCTTTCCTCCTGTACATAATGTCACTGGCTTGTTGGGATTTTTAATTTATCTTCACTCAGCACCA   2920

AGGGCCCCCGACACTCCACTCCTGCTGCCCCTGAGCTGAGCAGAGTCATTATTGGAGAGTTTTGTATTTATTAAAACAT   2999

TTCTTTTTCAGTCAAAAAAAAAAAAAAAAGGGCGGCCGC
                                                                                    3037
```

FIG. 1C

```
APPAPLLLLGLLLLGSRPARGAGPEPPVLPIRSEKEPLPVRGAAGCTFGG  60
..|: ||::.|:::        |.::.....|||..|.|||. :.:|||||||
QCPPILLVWTLWIM....AVDCSRPKVFLPIQPEQEPLQSKTPAGCTFGG  47

KVYALDETWHPDLGEPFGVMRCVLCACEAPQWGRRTRGPGRVSCKNIKPE 110
|.|.|::.|||||||||||:||||  ||  ||::||.:..|:|||||||.:
KFYSLEDSWHPDLGEPFGVMHCVLCYCE.PQRSRRGKPSGKVSCKNIKHD  96

CPTPACGQPRQLPGHCCQTCPQERSSSERQPSGL..SFEYPRDPEHRSYS 158
||.|.|:.|  ||  |||.|||......:...  :  :|||  .:.:.   |.
CPSPSCANPILLPLHCCKTCPKAPPPPIKKSDFVFDGFEYFQEKDDDLYN 146

DRGEPGAEERARGDGHTDFVALLTGPR......SQAVARARVSLLRSSLR 202
||:   :.:: |  :::::..::|||||:|.       .:||:||..| ||.|
DRSYLSSDDVAVEESRSEYVALLTAPSHVWPPVTSGVAKARFNLQRSNLL 196

FSISYRRLDRPTRIRFSDSNGSVLFEHPA...APTQDGLVCGVWRAVPRL 249
|||.|:::||  .|||||| :|||||||.       :...|: :||:||.: |
FSITYKWIDRLSRIRFSDLDGSVLFEHPVHRMGSPRDDTICGIWRSLNRS 246

SLRLLRAEQLHVALVTLTHPSGEVWGPLIRHRALAAETFSAILTLEGPPQ 299
.|||||  :::  |.|||  |  ...|:.|.:::|:||  .|.|||:||  |:..:
TLRLLRMGHILVSLVTTTLSEPEISGKIVKHKALFSESFSALLTPEDSDE 296

QGVGGITLLTLSDTEDSLHFLLLFRGLLEPRSGGLTQVPLRLQILHQGQL 349
|.||:.:|||||.:|.|||:::|||  :. ::      |:|: :|| ||.::
TGGGGLAMLTLSDVDDNLHFILMLRGLSGEEGD...QIPILVQISHQNHV 343

LRELQANVSAQEPGFAEVLPNLTVQEMDWLVLGELQMALEWAGRPGLRIS 399
:|||  ||:||||.:|||||:|.  .|| ||.  |:|::.::  .||.. .:|
IRELYANISAQEQDFAEVLPDLSSREMLWLAQGQLEISVQTEGRRPQSMS 393

GHIAARKSCDVLQSVLCGADALIPVQTGAAGSASLTLLGNGSLIYQVQVV 449
| |..|||||.|||||:|:|||  |..|||.||||:||   :||.| ||:|:.
GIITVRKSCDTLQSVLSGGDALNPTKTGAVGSASITLHENGTLEYQIQIA 443
```

FIG. 2A

```
GTSSEVVAMTLETKPQRRDQRTVLCHMAGLQPGGHTAVGICPGLGARGAH 499
|| |.|.|:||||||.|:..|.:| .|.   .:|: . |.  : .||: |
GTMSTVTAVTLETKPRRKTKRNILHDMSKDYHDGR.VWGYWIDANARDLH 492

MLLQNELFLNVGTKDFPDGELRGHVAALPYCGHSARHDTLSVPLAGALVL 549
||||.||||||:||||.:||||::.:| |:| .||.:.|.|||||.:|
MLLQSELFLNVATKDFQEGELRGQITPLLYSGLWARYEKLPVPLAGQFVS 542

PPVKSQAAGHAWLSLDTHCHLHYEVLLVGLGGSEQGTVTAHLLG...... 593
||::...|||||:|||.||||||::::.||| .|::.:.||| |
PPIRTGSAGHAWVSLDEHCHLHYQIVVTGLGKAEDAALNAHLHGFAELGE 592

.PPGTPGPRRLLKGFYGSEAQGVVKDLEPELLRHLAKGMASLMITTKGSP 642
..:.||.:|||||||||||| ||||: ||| ||.:| | : :.|| .|
VGESSPGHKRLLKGFYGSEAQGSVKDLDLELLGHLSRGTAFIQVSTKLNP 642

RGELRG............................................ 648
|||:||
RGEIRGQIHIPNSCESGGVSLTPEEPEYEYEIYEEGRQRDPDDLRKDPRA 692

.........................QRRTVICDPVVCPPPSCPHPVQA 671
                         |:|||||||:||||  .|.:||:
CSFEGQLRAHGSRWAPDYDRKCSVCSCQKRTVICDPIVCPPLNCSQPVHL 742

PDQCCPVCPEKQDVRDLPGLPRSRDPGEGCYFDGDRSWRAAGTRWHPVVP 721
||||||||.||.:|:..  .|.| .:|||:|||||||:||||||||.||
PDQCCPVCEEKKEMREVKKPERAR.TSEGCFFDGDRSWKAAGTRWHPFVP 791

PFGLIKCAVCTCKGGTGEVHCEKVQCPRLACAQPVRVNPTDCCKQCPVGS 771
||||||||:|||||:||||||||||||| ||:|.|..|:|.||.||||||:.
PFGLIKCAICTCKGSTGEVHCEKVTCPKLSCTNPIRANPSDCCKQCPVEE 841

GAHPQLGDPMQADGPRGCRFAGQWFPESQSWHPSVPPFGEMSCITCRCGA 821
.. :|:|.||.||: :|||: :|:|: :.|||.|||||||.|:|| |:.
RSPMELADSMQSDGAGSCRFGRHWYPNHERWHPTVPPFGEMKCVTCTCAE 891

GVPHCERDDCSLPLSCGSGKESRCCSRC......TAHRRPAPETRTDPEL 865
|:..| |::|. . :...:| .|||.:|       ...: ...||||. .:
GITQCRRQECTGTTCGTGSKRDRCCTKCKDANQDEDEKVKSDETRTPWSF 941
```

FIG. 2B

HUCHORDIN AND USES THEREOF

SUMMARY OF THE INVENTION

The invention relates to the discovery and characterization of a new human gene, huchordin, and huchordin polypeptides. Northern blot analysis of huchordin mRNA reveals that the huchordin gene is expressed as an approximately 7.5 kb transcript in adult and fetal liver and as an approximately 4.4 kb transcript in adult brain, heart, and pancreas. An additional approximately 2.7 kb transcript is observed in fetal liver.

A cDNA corresponding to huchordin has been cloned (SEQ ID NO:1). Nucleotides 1 to 2601 (SEQ ID NO:1) of this cDNA encode an 867 amino acid protein (SEQ ID NO:2) that has homology to Xenopus chordin (Sasai et al., *Cell* 79:779, 1994).

The invention encompasses nucleic acids that have a sequence that is substantially identical to a huchordin nucleic acid sequence. A nucleic acid which is substantially identical to a given reference nucleic acid molecule is hereby defined as a nucleic acid having a sequence that has at least 85%, preferably 90%, and more preferably 95%, 98%, 99% or more identity to the sequence of the given reference nucleic acid molecule, e.g., the nucleic acid sequence of SEQ ID NO:1.

A polypeptide or nucleic acid molecule which is "substantially identical" to a given reference polypeptide or nucleic acid molecule is a polypeptide or nucleic acid molecule having a sequence that has at least 85%, preferably 90%, and more preferably 95%, 98%, 99% or more identity to the sequence of the given reference polypeptide sequence or nucleic acid molecule, e.g., the polypeptide sequence of SEQ ID NO:2 or the nucleic acid sequence of SEQ ID NO:1.

The nucleic acid molecules of the invention can be inserted into vectors, described below, which will facilitate expression of the gene. The nucleic acid molecules and polypeptides of the invention can be used directly as diagnostic or therapeutic agents, or (in the case of a polypeptide) can be used to generate antibodies that, in turn, are therapeutically useful. Accordingly, expression vectors containing the nucleic acid molecules of the invention, cells transfected with these vectors, the polypeptides expressed by these vectors, and antibodies generated against either the entire polypeptide or an antigenic fragment thereof are among the preferred embodiments.

A transformed cell is any cell into which (or into an ancestor of which) has been introduced, by means of recombinant DNA techniques, a nucleic acid molecule encoding a polypeptide of the invention (e.g., a huchordin polypeptide).

An isolated nucleic acid molecule is a nucleic acid molecule that is separated from the 5' and 3' coding sequences with which it is immediately contiguous in the naturally occurring genome of an organism. Isolated nucleic acid molecules include nucleic acid molecule which are not naturally occurring, e.g., nucleic acid molecules created by recombinant DNA techniques.

Nucleic acid molecules include both RNA and DNA, including cDNA, genomic DNA, and synthetic (e.g., chemically synthesized) DNA. Where single-stranded, the nucleic acid molecule may be a sense strand or an antisense strand.

The invention also encompasses nucleic acid molecules that hybridize, preferably under stringent conditions, to a nucleic acid molecule encoding a huchordin polypeptide (e.g., a nucleic acid molecule having the sequence shown in SEQ ID NO:1 (nucleotides 1 to 2601 of SEQ ID NO:1), a nucleic acid molecule having the sequence of the huchordin encoding portion of the sequence of SEQ ID NO:1), or a nucleic acid molecule having the sequence of the protein coding portion of ATCC deposit No. 98481. Preferably the hybridizing nucleic acid molecule consists of 400, more preferably 200 nucleotides. Preferred hybridizing nucleic acid molecules have a biological activity possessed by huchordin.

The invention also features substantially pure or isolated huchordin polypeptides, including those that correspond to various functional domains of huchordin, or fragments thereof. The polypeptides of the invention encompass amino acid sequences that are substantially identical to the amino acid sequence shown in FIGS. 1A–1C (SEQ ID NO:2).

The polypeptides of the invention can also be chemically synthesized, or they can be purified from tissues in which they are naturally expressed, according to standard biochemical methods of purification.

Also included in the invention are functional polypeptides which possess one or more of the biological functions or activities of huchordin. These functions include the ability to bind some or all of the proteins which normally bind to huchordin. A functional polypeptide is also considered within the scope of the invention if it serves as an antigen for production of antibodies that specifically bind to huchordin. In many cases, functional polypeptides retain one or more domains present in the naturally-occurring form of the polypeptide.

The functional polypeptides may contain a primary amino acid sequence that has been modified from those disclosed herein. Preferably these modifications consist of conservative amino acid substitutions, as described herein.

The terms "protein" and "polypeptide" are used herein to describe any chain of amino acids, regardless of length or post-translational modification (for example, glycosylation or phosphorylation). Thus, the term "huchordin polypeptides" includes full-length, naturally occurring huchordin protein, as well a recombinantly or synthetically produced polypeptide that corresponds to a full-length, naturally occurring huchordin protein or to particular domains or portions of a naturally occurring protein. The term also encompasses mature huchordin which has an added amino-terminal methionine (useful for expression in prokaryotic cells).

The term "purified" as used herein refers to a nucleic acid or peptide that is substantially free of cellular material, viral material, or culture medium when produced by recombinant DNA techniques, or chemical precursors or other chemicals when chemically synthesized.

Polypeptides or other compounds of interest are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide.

It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

The invention also features antibodies, e.g., monoclonal, polyclonal, and engineered antibodies, which specifically bind huchordin. By "specifically binds" is meant an antibody that recognizes and binds to a particular antigen, e.g., a huchordin polypeptide of the invention, but which does not substantially recognize or bind to other molecules in a sample, e.g., a biological sample, which includes huchordin.

The invention also features antagonists and agonists of huchordin that can inhibit or enhance, respectively, one or more of the biological activities of huchordin. Suitable antagonists can include small molecules (i.e., molecules with a molecular weight below about 500), large molecules (i.e., molecules with a molecular weight above about 500), antibodies that bind and "neutralize" huchordin (as described below), polypeptides which compete with a native form of huchordin for binding to a protein, e.g., a member of the TGF-β superfamily, and nucleic acid molecules that interfere with transcription of huchordin (for example, antisense nucleic acid molecules and ribozymes). Agonists of huchordin also include small and large molecules, and antibodies other than neutralizing antibodies.

The invention also features molecules which can increase or decrease the expression of huchordin (e.g., by influencing transcription or translation). Small molecules (i.e., molecules with a molecular weight below about 500), large molecules (i.e., molecules with a molecular weight above about 500), and nucleic acid molecules that can be used to inhibit the expression of huchordin (for example, antisense and ribozyme molecules) or to enhance the expression of huchordin (for example, molecules that bind to a huchordin transcription regulatory sequence and increase huchordin transcription).

The invention also features molecules which alter the cellular localization of huchordin. Such molecules can be used to treat disorders associated with aberrant cellular localization of huchordin.

In addition, the invention features substantially pure polypeptides that functionally interact with huchordin, e.g., novel members of the TGF-β superfamily, and the nucleic acid molecules that encode them.

The invention encompasses methods for treating disorders associated with aberrant expression, activity or localization of huchordin. Thus, the invention includes methods for treating disorders associated with excessive expression or activity of huchordin. Such methods entail administering a compound which decreases the expression or activity of huchordin. The invention also includes methods for treating disorders associated with insufficient expression or activity of huchordin. These methods entail administering a compound which increases the expression or activity of huchordin.

The invention also features methods for detecting a huchordin polypeptide. Such methods include: obtaining a biological sample; contacting the sample with an antibody that specifically binds huchordin under conditions which permit specific binding; and detecting any antibody-huchordin complexes formed.

In addition, the present invention encompasses methods and compositions for the diagnostic evaluation, typing, and prognosis of disorders associated with inappropriate expression or activity of huchordin. For example, the nucleic acid molecules of the invention can be used as diagnostic hybridization probes to detect, for example, inappropriate expression of huchordin or mutations in the huchordin gene. Such methods may be used to classify cells by the level of huchordin expression.

Thus, the invention features a method for diagnosing a disorder associated with aberrant activity of huchordin, the method including obtaining a biological sample from a patient and measuring huchordin activity in the biological sample, wherein increased or decreased huchordin activity in the biological sample compared to a control indicates that the patient suffers from a disorder associated with aberrant activity of huchordin.

The present invention further provides for diagnostic kits for the practice of such methods.

The invention features methods of identifying compounds that modulate the expression or activity of huchordin by assessing the expression or activity of huchordin in the presence and absence of a selected compound. A difference in the level of expression or activity of huchordin in the presence and absence of the selected compound indicates that the selected compound is capable of modulating expression or activity or huchordin. Expression can be assessed either at the level of gene expression (e.g., by measuring mRNA) or protein expression by techniques that are well known to skilled artisans. The activity of huchordin can be assessed functionally.

Also included in the invention are: a method for detecting huchordin in a sample, the method including:

(a) obtaining a biological sample;

(b) contacting the biological sample with an antibody that specifically binds huchordin under conditions that allow the formation of huchordin-antibody complexes; and (c) detecting the complexes, if any, as an indication of the presence of huchordin in the sample.

In another aspect, the invention features a method of identifying a compound that modulates the activity of huchordin, the method including comparing the level of activity of huchordin in a cell in the presence and absence of a selected compound, wherein a difference in the level of activity in the presence and absence of the selected compound indicates that the selected compound modulates the activity of huchordin.

The invention also features a method for diagnosing a disorder associated with aberrant expression of huchordin, the method including obtaining a biological sample from a patient and measuring huchordin expression in the biological sample, wherein increased or decreased huchordin expression in the biological sample compared to a control indicates that the patient suffers from a disorder associated with aberrant expression of huchordin.

In another aspect the invention features a method for diagnosing a disorder associated with aberrant activity of huchordin, the method including obtaining a biological sample from a patient and measuring huchordin activity in the biological sample, wherein increased or decreased huchordin activity in the biological sample compared to a control indicates that the patient suffers from a disorder associated with aberrant activity of huchordin.

The preferred methods and materials are described below in examples which are meant to illustrate, not limit, the invention. Skilled artisans will recognize methods and materials that are similar or equivalent to those described herein, and that can be used in the practice or testing of the present invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described herein. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the detailed description, and from the claims.

BRIEF DESCRIPTION OF THE DRAWING

FIGS. 1A–1C is a depiction of the sequence of a cDNA encoding huchordin (SEQ ID NO:1) and the deduced amino sequence (SEQ ID NO:2) of huchordin.

FIGS. 2A–2B is an alignment of a portion of the amino acid sequence of huchordin (upper sequence of each pair) and a portion of amino acid sequence of Xenopus chordin (lower sequence of each pair; SEQ ID NO:4).

DETAILED DESCRIPTION

Huchordin, a human protein described here for the first time, is a 867 amino acid protein that is predicted to be a secreted protein. A putative signal sequence encompasses amino acids 1–26 of huchordin.

Huchordin bears homology to Xenopus chordin (Sasai et al., *Cell* 79:779, 1994). Like Xenopus chordin, huchordin includes several cysteine-rich repeats. Xenopus chordin includes four such repeats (R1, R2, R3, and R4) of 58–74 residues (Sasai et al., *Cell* 79:779, 1994) each of which includes 10 cysteine residues at conserved positions.

Huchordin contains three intact cysteine-rich repeats (amino acids 51–125; amino acids 696–762; and amino acids 784–844), corresponding to R1, R3, and R4 of chordin. The huchordin cysteine-rich repeat (amino acids 644–674) corresponding to R2 of chordin contains only six of the 10 conserved cys residues and is properly considered a half repeat.

Four potential N-glycosylation sites (217, 351, 365, and 434) are located between R1 and R2 in huchordin. Chordin also has four such sites. Two of the potential huchordin N-glycosylation sites N351 at N434 are in positions that are conserved in chordin.

Overall, the huchordin gene described herein has 66% homology at the nucleotide level to the Xenopus chordin gene, and the huchordin protein described herein has 53% homology to Xenopus chordin protein at the amino acid level.

Huchordin Nucleic Acid Molecules

The huchordin nucleic acid molecules of the invention can be cDNA, genomic DNA, synthetic DNA, or RNA, and can be double-stranded or single-stranded (i.e., either a sense or an antisense strand). Fragments of these molecules are also considered within the scope of the invention, and can be produced, for example, by the polymerase chain reaction (PCR) or generated by treatment with one or more restriction endonucleases. A ribonucleic acid (RNA) molecule encoding huchordin can be produced by in vitro transcription.

The nucleic acid molecules of the invention can contain naturally occurring sequences, or sequences that differ from those that occur naturally, but, due to the degeneracy of the genetic code, encode the same polypeptide (for example, the polypeptide of SEQ ID NO:2). In addition, these nucleic acid molecules are not limited to sequences that only encode polypeptides, and thus, can include some or all of the non-coding sequences that lie upstream or downstream from the huchordin coding sequence.

The nucleic acid molecules of the invention can be synthesized (for example, by phosphoramidite-based synthesis) or obtained from a biological cell (e.g., by cDNA cloning), such as the cell of a mammal. Thus, the nucleic acids can be those of a human, mouse, rat, guinea pig, cow, sheep, horse, pig, rabbit, monkey, dog, or cat. Combinations or modifications of the nucleotides within these types of nucleic acids are also encompassed.

In addition, the isolated nucleic acid molecules of the invention encompass fragments that are not found as such in the natural state. Thus, the invention encompasses recombinant molecules, such as those in which a nucleic acid molecule (for example, an isolated nucleic acid molecule encoding huchordin) is incorporated into a vector (for example, a plasmid or viral vector) or into the genome of a heterologous cell (or the genome of a homologous cell, at a position other than the natural chromosomal location). Recombinant nucleic acid molecules and uses therefor are discussed further below.

The invention encompasses peptide nucleic acids (PNA) and PNA-DNA chimeras having the sequence of a portion of the huchordin gene. DNA oligomers and PNA-DNA chimeric oligmers can be used for antisense inhibition (i.e., inhibition of translation) and anti-gene inhibition (i.e., inhibition of transcription) (Hyrup et al., *Bioorganic & Medicinal Chem.* 4:5, 1996; Finn et al., Nucl. Acids Res. 24: 33357, 1996). PNA oligomer can also be used in DNA pre-gel hybridization as an alternative to Southern hybridization.

In the event the nucleic acid molecules of the invention encode or act as antisense molecules, they can be used for example, to regulate translation of huchordin mRNA. Techniques associated with the use of huchordin nucleic acid molecules for detection or regulation of huchordin expression can be used to diagnose and/or treat disorders associated with aberrant huchordin expression. These nucleic acid molecules are discussed further below in the context of their clinical utility.

The invention encompasses single-stranded nucleic acid probes which hybridize to a huchordin nucleic acid molecule (e.g., the nucleic acid molecule of SEQ ID NO:1). Such probes can be used diagnostic methods to detect mutations in the huchordin gene. For example, probes can be used to create a high density oligonucleotide probe array which can be used diagnostically to detect mutations and allelic variations in the huchordin gene (Cronin et al., *Human Mutation* 7:244, 1996).

Also within the invention are single-stranded nucleic acid primers which can be used to PCR amplify all or part of a huchordin-encoding nucleic acid molecule.

The invention also encompasses nucleic acid molecules that hybridize under stringent conditions to a nucleic acid molecule encoding a huchordin polypeptide. The protein encoding portion of the cDNA sequence described herein (SEQ ID NO:1) can be used to identify these nucleic acid molecules, which include, for example, nucleic acids that encode homologous polypeptides in other mammalian species, splice variants of the huchordin gene in humans or other mammals, and allelic variants of the huchordin gene or the genes encoding homologs of huchordin in other mammals (a naturally-occurring mammalian gene). Further, genes may exist at other genetic loci within the genome that encode proteins which have extensive homology to huchordin polypeptides or one or more domains of huchordin polypeptides. Accordingly, the invention features methods of detecting and isolating these nucleic acid molecules. Using these methods, a sample (for example, a nucleic acid library, such as a cDNA or genomic library) is contacted (or "screened") with a huchordin-specific probe (for example, a fragment of SEQ ID NO:1 that is at least 25 or 50 nucleotides long). The probe will selectively hybridize to nucleic acids encoding related polypeptides (or to complementary sequences thereof). The term "selectively hybridize" is used to refer to an event in which a probe binds to nucleic acids encoding huchordin (or to complementary sequences thereof) to a detectably greater extent than to nucleic acids encoding Xenopus chordin. The probe, which can contain at least 25 (for example, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., N.Y., 1989). For example, the probe can be generated using PCR amplification methods in which oligonucleotide primers are used to amplify a huchordin-specific nucleic acid sequence that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecyl-sulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2×SSC.

As an alternative to screening a cDNA library, a human total genomic DNA library can be screened using huchordin probes. Huchordin-positive clones can then be sequenced and, further, the intron/exon structure of the human huchordin gene can be elucidated. Once genomic sequence is obtained, oligonucleotide primers can be designed based on the sequence for use in the isolation, via, for example, Reverse Transcriptase-coupled PCR, of huchordin splice variants.

Further, a previously unknown gene sequence can be isolated by performing PCR using two degenerate oligonucleotide primer pools designed on the basis of nucleotide sequences within the huchordin cDNAs defined herein. The template for the reaction can be cDNA obtained by reverse transcription of mRNA prepared from human or non-human cell lines or tissue known or suspected to express a huchordin gene allele. The PCR product can be subcloned and sequenced to insure that the amplified sequences represent the sequences of a huchordin-like gene nucleic acid sequence.

The PCR fragment can then be used to isolate a full length cDNA clone by a variety of methods. For example, the amplified fragment can be labeled and used to screen a bacteriophage cDNA library. Alternatively, the labeled fragment can be used to screen a genomic library.

PCR technology also can be used to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of useful cloning strategies, see e.g., Sambrook et al., supra; and Ausubel et al., supra.

In cases where the gene identified is the normal (wild type) gene, this gene can be used to isolate mutant alleles of the gene. Such an isolation is preferable in processes and disorders which are known or suspected to have a genetic basis.

A cDNA of a mutant gene can be isolated, for example, by using PCR, a technique which is well-known to one skilled in the art. In this case, the first cDNA strand can be synthesized by hybridizing a oligo-dT oligonucleotide to mRNA isolated from tissue known or suspected of being expressed in an individual putatively carrying the mutant allele, and by extending the new strand with reverse transcriptase. The second strand of the cDNA can then be synthesized using an oligonucleotide that hybridizes specifically to the 5'-end of the normal gene. Using these two primers, the product is then amplified via PCR, cloned into a suitable vector, and subjected to DNA sequence analysis by methods well known in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probe to identify the corresponding mutant allele in the library. The clone containing this gene can then be purified through methods routinely practiced in the art, and subjected to sequence analysis using standard techniques as described herein.

Additionally, an expression library can be constructed using DNA isolated from or cDNA synthesized from a tissue known to or suspected of expressing the gene of interest in an individual suspected of or known to carry the mutant allele. In this manner, gene products made by the putatively mutant tissue can be expressed and screened using standard antibody screening techniques in conjunction with antibodies raised against the normal gene product, as described herein. For screening techniques, see, for example, Harlow, E. and Lane, eds., 1988, "Antibodies: A Laboratory Manual," Cold Spring Harbor Press, Cold Spring Harbor.

In cases where the mutation results in an expressed gene product with altered function (e.g., as a result of a missense mutation), a polyclonal set of antibodies is likely to cross-react with the mutant gene product. Library clones detected via their reaction with such labeled antibodies can be purified and subjected to sequence analysis as described herein.

Once detected, the nucleic acid molecules can be isolated by any of a number of standard techniques (see, for example, Sambrook et al., "Molecular Cloning, A Laboratory Manual," 2nd Ed. Cold Spring Harbor Laboratory Press, Cold Spring Harbor, N.Y., 1989).

The invention also encompasses: (a) expression vectors that contain any of the foregoing huchordin-related coding sequences and/or their complements (that is, "antisense" sequence); (b) expression vectors that contain any of the foregoing huchordin-related coding sequences operatively associated with a regulatory element (examples of which are given below) that directs the expression of the coding sequences; (c) expression vectors containing, in addition to sequences encoding a huchordin polypeptide, nucleic acid sequences that are unrelated to nucleic acid sequences encoding huchordin, such as molecules encoding a reporter, a marker, or a portion of an immunoglobin; and (d) genetically engineered host cells that contain any of the foregoing expression vectors and thereby express the nucleic acid molecules of the invention in the host cell.

Recombinant nucleic acid molecules can contain a sequence encoding a soluble huchordin polypeptide, mature huchordin (e.g., amino acids 27–867 of SEQ ID NO:2), or huchordin having a signal sequence. The full length huchordin polypeptide, a domain of huchordin, or a fragment thereof may be fused to additional polypeptides, as described below. Similarly, the nucleic acid molecules of the invention can encode the mature form of huchordin or a form that encodes a polypeptide which facilitates secretion. In the latter instance, the polypeptide is typically referred to as a proprotein, which can be converted into an active form by removal of the signal sequence, for example, within the host cell.

The regulatory elements referred to above include, but are not limited to, inducible and non-inducible promoters, enhancers, operators and other elements, which are known to those skilled in the art, and which drive or otherwise regulate gene expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

Similarly, the nucleic acid can form part of a hybrid gene encoding additional polypeptide sequences, for example, sequences that function as a marker or reporter. Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-phosphotransferase (HPH), thymidine kinase (TK), lacZ (encoding β-galactosidase), and xanthine guanine phosphoribosyltransferase (XGPRT). As with many of the standard procedures associated with the practice of the invention, skilled artisans will be aware of additional useful reagents, for example, of additional sequences that can serve the function of a marker or reporter. Generally, the hybrid polypeptide will include a first portion and a second portion; the first portion being a huchordin polypeptide and the second portion being, for example, the reporter described above or an immunoglobulin constant region.

The expression systems that may be used for purposes of the invention include, but are not limited to, microorganisms such as bacteria (for example, E. coli and B. subtilis) transformed with recombinant bacteriophage DNA, plasmid DNA, or cosmid DNA expression vectors containing the nucleic acid molecules of the invention; yeast (for example, Saccharomyces and Pichia) transformed with recombinant yeast expression vectors containing the nucleic acid molecules of the invention (preferably containing the nucleic acid sequence encoding huchordin (contained within SEQ ID NO:2)); insect cell systems infected with recombinant virus expression vectors (for example, baculovirus) containing the nucleic acid molecules of the invention; plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing huchordin nucleotide sequences; or mammalian cell systems (for example, COS, CHO, BHK, 293, VERO, HeLa, MDCK, WI38, and NIH 3T3 cells) harboring recombinant expression constructs containing promoters derived from the genome of mammalian cells (for example, the metallothionein promoter) or from mammalian viruses (for example, the adenovirus late promoter and the vaccinia virus 7.5K promoter).

In bacterial systems, a number of expression vectors may be advantageously selected depending upon the use intended for the gene product being expressed. For example, when a large quantity of such a protein is to be produced, for the generation of pharmaceutical compositions containing huchordin polypeptides or for raising antibodies to those polypeptides, vectors that are capable of directing the expression of high levels of fusion protein products that are readily purified may be desirable. Such vectors include, but are not limited to, the *E. coli* expression vector pUR278 (Ruther et al., *EMBO J.* 2:1791, 1983), in which the coding sequence of the insert may be ligated individually into the vector in frame with the lacZ coding region so that a fusion protein is produced; pIN vectors (Inouye and Inouye, *Nucleic Acids Res.* 13:3101–3109, 1985; Van Heeke and Schuster, *J. Biol. Chem.* 264:5503–5509, 1989); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhidrosis virus (AcNPV) can be used as a vector to express foreign genes. The virus grows in *Spodoptera frugiperda* cells. The coding sequence of the insert may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (for example, see Smith et al., *J. Virol.* 46:584, 1983; Smith, U.S. Pat. No. 4,215,051).

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a huchordin gene product in infected hosts (for example, see Logan and Shenk, *Proc. Natl. Acad. Sci. USA* 81:3655–3659, 1984).

Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signals may be needed. However, in cases where only a portion of the coding sequence is inserted, e.g., only the portion encoding the mature form of a secreted protein, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:516–544, 1987).

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

For long-term, high-yield production of recombinant proteins, stable expression is preferred. For example, cell lines which stably express the huchordin sequences described above may be engineered. Rather than using expression vectors which contain viral origins of replication, host cells can be transformed with DNA controlled by appropriate expression control elements (for example, promoter, enhancer sequences, transcription terminators, polyadenylation sites, etc.), and a selectable marker. Following the introduction of the foreign DNA, engineered cells may be allowed to grow for 1-2 days in an enriched media, and then switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express huchordin. Such engineered cell lines may be particularly useful in screening and evaluation of compounds that affect the endogenous activity of the gene product.

A number of selection systems can be used. For example, the herpes simplex virus thymidine kinase (Wigler, et al., Cell 11:223, 1977), hypoxanthine-guanine phosphoribosyltransferase (Szybalska and Szybalski, Proc. Natl. Acad. Sci. USA 48:2026, 1962), and adenine phosphoribosyltransferase (Lowy, et al., Cell 22:817, 1980) genes can be employed in tk⁻, hgprt⁻ or aprt⁻ cells, respectively. Also, anti-metabolite resistance can be used as the basis of selection for the following genes: dhfr, which confers resistance to methotrexate (Wigler et al., Proc. Natl. Acad. Sci. USA 77:3567, 1980; O'Hare et al., Proc. Natl. Acad. Sci. USA 78:1527, 1981); gpt, which confers resistance to mycophenolic acid (Mulligan and Berg, Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1984).

Huchordin nucleic acid molecules are useful for diagnosis of disorders associated with aberrant expression of huchordin. Huchordin nucleic acid molecules are also useful in genetic mapping and chromosome identification.

Huchordin Polypeptides

The huchordin polypeptides described herein are those encoded by any of the nucleic acid molecules described above and include huchordin fragments, mutants, truncated forms, and fusion proteins. These polypeptides can be prepared for a variety of uses, including but not limited to the generation of antibodies, as reagents in diagnostic assays, for the identification of other cellular gene products or compounds that can modulate the activity or expression of huchordin, and as pharmaceutical reagents useful for the treatment of disorders associated with aberrant expression or activity of huchordin.

Preferred polypeptides are substantially pure huchordin polypeptides, including those that correspond to the polypeptide with and without intact signal sequence Especially preferred are huchordin polypeptides that are soluble under normal physiological conditions.

The invention also encompasses polypeptides that are functionally equivalent to huchordin. These polypeptides are equivalent to huchordin in that they are capable of carrying out one or more of the functions of huchordin in a biological system. Preferred huchordin polypeptides have 20%, 40%, 50%, 75%, 80%, or even 90% of one or more of the biological activities of the full-length, mature human form of huchordin. Such comparisons are generally based on an assay of biological activity in which equal concentrations of the polypeptides are used and compared. The comparison can also be based on the amount of the polypeptide required to reach 50% of the maximal stimulation obtainable.

Functionally equivalent proteins can be those, for example, that contain additional or substituted amino acid residues. Substitutions may be made on the basis of similarity in polarity, charge, solubility, hydrophobicity, hydrophilicity, and/or the amphipathic nature of the residues involved. Amino acids that are typically considered to provide a conservative substitution for one another are specified in the summary of the invention.

Polypeptides that are functionally equivalent to huchordin can be made using random mutagenesis techniques well known to those skilled in the art (and the resulting mutant huchordin proteins can be tested for activity). It is more likely, however, that such polypeptides will be generated by site-directed mutagenesis (again using techniques well known to those skilled in the art). These polypeptides may have increased functionality or decreased functionality.

To design functionally equivalent polypeptides, it is useful to distinguish between conserved positions and variable positions. This can be done by aligning the sequence of huchordin cDNAs that were obtained from various organisms. Conserved resides can also be identified by aligning motifs within huchordin. For example, the cys residues of the cys-rich repeats are conserved residues. Skilled artisans will recognize that conserved amino acid residues are more likely to be necessary for preservation of function. Thus, it is preferable that conserved residues are not altered.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Mutations within the huchordin coding sequence can be made to generate variant huchordin genes that are better suited for expression in a selected host cell. For example, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences which occur (in N—X—S or N—X—), and/or an amino acid deletion at the second position of any one or more of such recognition sequences, will prevent glycosylation at the modified tripeptide sequence (see, for example, Miyajima et al., EMBO J. 5:1193, 1986).

The polypeptides of the invention can be expressed fused to another polypeptide, for example, a marker polypeptide or fusion partner. Alternatively, a fusion protein may be readily purified by utilizing an antibody specific for the fusion protein being expressed. For example, a system described by Janknecht et al. allows for the ready purification of non-denatured fusion proteins expressed in human cell lines (Proc. Natl. Acad. Sci. USA 88: 8972–8976, 1991). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

The polypeptides of the invention can be chemically synthesized (for example, see Creighton, "Proteins: Structures and Molecular Principles," W. H. Freeman & Co., NY, 1983), or, perhaps more advantageously, produced by recombinant DNA technology as described herein. For additional guidance, skilled artisans may consult Ausubel et al. (supra), Sambrook et al. ("Molecular Cloning, A Laboratory Manual," Cold Spring Harbor Press, Cold Spring Harbor, N.Y., 1989), and, particularly for examples of chemical synthesis Gait, M. J. Ed. ("Oligonucleotide Synthesis," IRL Press, Oxford, 1984).

Once the recombinant huchordin protein is expressed, it is isolated. Secreted forms can be isolated from the culture media, while non-secreted forms must be isolated from the host cells. Proteins can be isolated by affinity chromatography. In one example, an anti-huchordin protein antibody (e.g., produced as described herein) is attached to a column and used to isolate the huchordin protein. Lysis and fractionation of huchordin protein-harboring cells prior to affinity chromatography can be performed by standard methods (see, e.g., Ausubel et al., supra). Alternatively, a huchordin fusion protein, for example, a huchordin-maltose binding protein, a huchordin-β-galactosidase, or a huchordin-trpE fusion protein, can be constructed and used for huchordin protein isolation (see, e.g., Ausubel et al., supra; New England Biolabs, Beverly, Mass.).

Once isolated, the recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

The invention also features polypeptides that interact with huchordin (and the genes that encode them) and thereby alter the function of huchordin. Interacting polypeptides can be identified using methods known to those skilled in the art. One suitable method is the "two-hybrid system," which detects protein interactions in vivo (Chien et al., *Proc. Natl. Acad. Sci. USA*, 88:9578, 1991). A kit for practicing this method is available from Clontech (Palo Alto, Calif.).

Transgenic Animals

Huchordin polypeptides can also be expressed in transgenic animals. These animals represent a model system for the study of disorders that are caused by or exacerbated by overexpression or underexpression of huchordin, and for the development of therapeutic agents that modulate the expression or activity of huchordin.

Transgenic animals can be farm animals (pigs, goats, sheep, cows, horses, rabbits, and the like) rodents (such as rats, guinea pigs, and mice), non-human primates (for example, baboons, monkeys, and chimpanzees), and domestic animals (for example, dogs and cats). Transgenic mice are especially preferred.

Any technique known in the art can be used to introduce a huchordin transgene into animals to produce the founder lines of transgenic animals. Such techniques include, but are not limited to, pronuclear microinjection (U.S. Pat. No. 4,873,191); retrovirus mediated gene transfer into germ lines (Van der Putten et al., *Proc. Natl. Acad. Sci., USA* 82:6148, 1985); gene targeting into embryonic stem cells (Thompson et al., *Cell* 56:313, 1989); and electroporation of embryos (Lo, *Mol. Cell. Biol.* 3:1803, 1983).

The present invention provides for transgenic animals that carry a the huchordin transgene in all their cells, as well as animals that carry a transgene in some, but not all of their cells. That is, the invention provides for mosaic animals. The transgene can be integrated as a single transgene or in concatamers, e.g., head-to-head tandems or head-to-tail tandems. The transgene can also be selectively introduced into and activated in a particular cell type (Lasko et al., *Proc. Natl. Acad. Sci. USA* 89:6232, 1992). The regulatory sequences required for such a cell-type specific activation will depend upon the particular cell type of interest, and will be apparent to those of skill in the art.

When it is desired that the huchordin transgene be integrated into the chromosomal site of the endogenous huchordin the endogenous, gene targeting is preferred. Briefly, when such a technique is to be used, vectors containing some nucleotide sequences homologous to an endogenous huchordin gene are designed for the purpose of integrating, via homologous recombination with chromosomal sequences, into and disrupting the function of the nucleotide sequence of the endogenous gene. The transgene also can be selectively introduced into a particular cell type, thus inactivating the endogenous huchordin gene in only that cell type (Gu et al., *Science* 265:103, 1984). The regulatory sequences required for such a cell-type specific inactivation will depend upon the particular cell type of interest, and will be apparent to those of skill in the art. These techniques are useful for preparing "knock outs" having no functional huchordin gene.

Once transgenic animals have been generated, the expression of the recombinant huchordin gene can be assayed utilizing standard techniques. Initial screening may be accomplished by Southern blot analysis or PCR techniques to determine whether integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and RT-PCR. Samples of huchordin gene-expressing tissue can also be evaluated immunocytochemically using antibodies specific for the huchordin transgene product.

For a review of techniques that can be used to generate and assess transgenic animals, skilled artisans can consult Gordon (*Intl. Rev. Cytol.* 115:171–229, 1989), and may obtain additional guidance from, for example: Hogan et al., "Manipulating the Mouse Embryo," Cold Spring Harbor Press, Cold Spring Harbor, N.Y., 1986; Krimpenfort et al., *Bio/Technology* 9:86, 1991; Palmiter et al., *Cell* 41:343, 1985; Kraemer et al., "Genetic Manipulation of the Early Mammalian Embryo," Cold Spring Harbor Press, Cold Spring Harbor, N.Y., 1985; Hammer et al., *Nature* 315:680, 1985; Purcel et al., *Science*, 244:1281, 1986; Wagner et al., U.S. Pat. No. 5,175,385; and Krimpenfort et al., U.S. Pat. No. 5,175,384 (the latter two publications are hereby incorporated by reference).

Anti-huchordin Antibodies

Huchordin polypeptides (or immunogenic fragments or analogs) can be used to raise antibodies useful in the invention; such polypeptides can be produced by recombinant techniques or synthesized (see, for example, "Solid Phase Peptide Synthesis," supra; Ausubel et al., supra). In general, the peptides can be coupled to a carrier protein, such as KLH, as described in Ausubel et al., supra, mixed with an adjuvant, and injected into a host mammal. Antibodies can be purified by peptide antigen affinity chromatography.

In particular, various host animals can be immunized by injection with a huchordin protein or polypeptide. Host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Potentially useful human adjuvants include BCG (bacille Calmette-Guerin) and Corynebacterium parvum. Polyclonal antibodies are heterogeneous populations of antibody molecules that are contained in the sera of the immunized animals.

Antibodies within the invention therefore include polyclonal antibodies and, in addition, monoclonal antibodies, humanized or chimeric antibodies, single chain antibodies, Fab fragments, F(ab')$_2$ fragments, and molecules produced using a Fab expression library.

Monoclonal antibodies, which are homogeneous populations of antibodies to a particular antigen, can be prepared using the huchordin polypeptides described above and standard hybridoma technology (see, for example, Kohler et al., *Nature* 256:495, 1975; Kohler et al., *Eur. J. Immunol.* 6:511, 1976; Kohler et al., *Eur. J. Immunol.* 6:292, 1976; Hammerling et al., "Monoclonal Antibodies and T Cell Hybridomas," Elsevier, N.Y., 1981; Ausubel et al., supra).

In particular, monoclonal antibodies can be obtained by any technique that provides for the production of antibody molecules by continuous cell lines in culture such as described in Kohler et al., *Nature* 256:495, 1975, and U.S. Pat. No. 4,376,110; the human B-cell hybridoma technique (Kosbor et al., *Immunology Today* 4:72, 1983; Cole et al., *Proc. Natl. Acad. Sci. USA* 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. The hybridoma producing the mAb of this invention may be cultivated in vitro or in vivo. The ability to produce high titers of mAbs in vivo makes this a particularly useful method of production.

Once produced, polyclonal or monoclonal antibodies are tested for specific huchordin recognition by Western blot or immunoprecipitation analysis by standard methods, e.g., as described in Ausubel et al., supra. Antibodies that specifically recognize and bind to huchordin are useful in the invention. For example, such antibodies can be used in an immunoassay to monitor the level of huchordin produced by a mammal (for example, to determine the amount or subcellular location of huchordin).

Preferably, antibodies of the invention are produced using fragments of the huchordin protein which lie outside highly conserved regions and appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

Antisera is also checked for its ability to immunoprecipitate recombinant huchordin proteins or control proteins, such as glucocorticoid receptor, CAT, or luciferase.

The antibodies can be used, for example, in the detection of the huchordin in a biological sample as part of a diagnostic assay. Antibodies also can be used in a screening assay to measure the effect of a candidate compound on expression or localization of huchordin. Additionally, such antibodies can be used in conjunction with the gene therapy techniques to, for example, evaluate the normal and/or engineered huchordin-expressing cells prior to their introduction into the patient. Such antibodies additionally can be used in a method for inhibiting abnormal huchordin activity.

In addition, techniques developed for the production of "chimeric antibodies" (Morrison et al., *Proc. Natl. Acad. Sci. USA*, 81:6851, 1984; Neuberger et al., *Nature*, 312:604, 1984; Takeda et al., *Nature*, 314:452, 1984) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. Nos. 4,946,778, 4,946,778, and 4,704,692) can be adapted to produce single chain antibodies against a huchordin protein or polypeptide. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Antibodies to huchordin can, in turn, be used to generate anti-idiotype antibodies that resemble a portion of huchordin using techniques well known to those skilled in the art (see, e.g., Greenspan et al., *FASEB J*. 7:437, 1993; Nissinoff, *J. Immunol.* 147:2429, 1991). For example, antibodies that bind to huchordin and competitively inhibit the binding of a binding partner of huchordin can be used to generate anti-idiotypic antibodies that resemble a binding partner binding domain of huchordin and, therefore, bind and neutralize a binding partner of huchordin. Such neutralizing anti-idiotypic antibodies or Fab fragments of such anti-idiotypic antibodies can be used in therapeutic regimens.

Antibodies can be humanized by methods known in the art. For example, monoclonal antibodies with a desired binding specificity can be commercially humanized (Scotgene, Scotland; Oxford Molecular, Palo Alto, Calif.). Fully human antibodies, such as those expressed in transgenic animals are also features of the invention (Green et al., *Nature Genetics* 7:13–21, 1994; see also U.S. Pat. Nos. 5,545,806 and 5,569,825, both of which are hereby incorporated by reference).

The methods described herein in which anti-huchordin antibodies are employed may be performed, for example, by utilizing pre-packaged diagnostic kits comprising at least one specific huchordin nucleotide sequence or antibody reagent described herein, which may be conveniently used, for example, in clinical settings, to diagnose patients exhibiting symptoms of the disorders described below.

Antisense Nucleic Acids

Treatment regimes based on an "antisense" approach involve the design of oligonucleotides (either DNA or RNA) that are complementary to huchordin mRNA. These oligonucleotides bind to the complementary huchordin mRNA transcripts and prevent translation. Absolute complementarity, although preferred, is not required. A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs recently have been shown to be effective at inhibiting translation of mRNAs as well (Wagner, *Nature* 372:333, 1984). Thus, oligonucleotides complementary to either the 5' or 3' non-translated, non-coding regions of the huchordin gene, e.g., the human gene shown in FIGS. 1A–1C could be used in an antisense approach to inhibit translation of endogenous huchordin mRNA. Oligonucleotides complementary to the 5' untranslated region of the mRNA should include the complement of the AUG start codon.

Antisense oligonucleotides complementary to mRNA coding regions are less efficient inhibitors of translation but could be used in accordance with the invention. Whether designed to hybridize to the 5', 3', or coding region of huchordin mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or PNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (as described, e.g., in Letsinger et al., *Proc. Natl. Acad. Sci. USA* 86:6553, 1989; Lemaitre et al., *Proc. Natl. Acad. Sci. USA* 84:648, 1987; PCT Publication No. WO 88/09810) or the blood-brain barrier (see, for example, PCT Publication No. WO 89/10134), or hybridization-triggered cleavage agents (see, for example, Krol et al., *BioTechniques* 6:958, 1988), or intercalating agents (see, for example, Zon, *Pharm. Res.* 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

In yet another embodiment, the antisense oligonucleotide is an a-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-0-methylribonucleotide (Inoue et al., *Nucl. Acids Res.* 15:6131, 1987), or a chimeric RNA-DNA analog (Inoue et al., *FEBS Lett.* 215:327, 1987).

Peptide nucleic acid (PNA) oligonucleotides can be used as antisense molecules (Hyrup et al., *Bioorganic & Medicinal Chem.* 4:5, 1996).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Natl. Acad. Sci. USA* 85:7448, 1988).

While antisense nucleotides complementary to the huchordin coding region sequence could be used, those complementary to the transcribed untranslated region are most preferred.

The antisense molecules should be delivered to cells that express huchordin in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, a preferred approach uses a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous huchordin transcripts and thereby prevent translation of the huchordin mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

Ribozymes

Ribozyme molecules designed to catalytically cleave huchordin mRNA transcripts also can be used to prevent translation of huchordin mRNA and expression of huchordin (see, e.g., PCT Publication WO 90/11364; Saraver et al., *Science* 247:1222, 1990). While various ribozymes that cleave mRNA at site-specific recognition sequences can be used to destroy huchordin mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). There are numerous examples of potential hammerhead ribozyme cleavage sites within the nucleotide sequence of human huchordin cDNA. Preferably, the ribozyme is engineered so that the cleavage recognition site is located near the 5' end of the huchordin mRNA, i.e., to increase efficiency and minimize the intracellular accumulation of non-functional mRNA transcripts.

The ribozymes of the present invention also include RNA endoribonucleases (hereinafter "Cech-type ribozymes"), such as the one that occurs naturally in *Tetrahymena Thermophila* (known as the IVS or L-19 IVS RNA), and which has been extensively described by Cech and his collaborators (Zaug et al., *Science* 224:574, 1984; Zaug et al., *Science*, 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in huchordin.

As in the antisense approach, the ribozymes can be composed of modified oligonucleotides (e.g., for improved stability, targeting, etc.), and should be delivered to cells which express the huchordin in vivo. A preferred method of delivery involves using a DNA construct "encoding" the ribozyme under the control of a strong constitutive pol III or pol II promoter, so that transfected cells will produce sufficient quantities of the ribozyme to destroy endogenous huchordin messages and inhibit translation. Because ribozymes, unlike antisense molecules, are catalytic, a lower intracellular concentration is required for efficiency.

Methods for Reducing Huchordin Expression

A variety of methods can be used to reduce huchordin expression. For example, the antisense techniques described above can be used to reduce huchordin expression.

Endogenous huchordin gene expression can also be reduced by inactivating or "knocking out" the huchordin gene or its promoter using targeted homologous recombination (see, e.g., U.S. Pat. No. 5,464,764). For example, a mutant, non-functional huchordin (or a completely unrelated DNA sequence) flanked by DNA homologous to the endogenous huchordin gene (either the coding regions or regulatory regions of the huchordin gene) can be used, with or without a selectable marker and/or a negative selectable marker, to transfect cells that express huchordin in vivo. Insertion of the DNA construct, via targeted homologous recombination, results in inactivation of the huchordin gene. Such approaches are particularly suited for use in the agricultural field where modifications to ES (embryonic stem) cells can be used to generate animal offspring with an inactive huchordin. However, this approach can be adapted for use in humans, provided the recombinant DNA constructs are directly administered or targeted to the required site in vivo using appropriate viral vectors.

Alternatively, endogenous huchordin gene expression can be reduced using deoxyribonucleotide sequences complementary to the regulatory region of the huchordin gene (i.e., the huchordin promoter and/or enhancers) to form triple helical structures that prevent transcription of the huchordin gene in target cells in the body (Helene *Anticancer Drug Res.* 6:569, 1981; Helene et al., *Ann. N.Y. Acad. Sci.* 660:27, 1992; and Maher, *Bioassays* 14:807, 1992) or through the use of small molecules which interfere with the expression or activity of transcription factors which regulate huchordin expression.

Detecting Proteins Associated with Huchordin

The invention also features polypeptides which interact with huchordin. Any method suitable for detecting protein-protein interactions may be employed for identifying transmembrane proteins, intracellular, or extracellular proteins that interact with huchordin. Among the traditional methods which may be employed are co-immunoprecipitation, crosslinking and co-purification through gradients or chromatographic columns of cell lysates or proteins obtained from cell lysates and the use of huchordin to identify proteins in the lysate that interact with huchordin. For these assays, the huchordin polypetide can be a full length huchordin, a soluble extracellular domain of huchordin, or some other suitable huchordin polypeptide. Once isolated, such an interacting protein can be identified and cloned and then used, in conjunction with standard techniques, to identify proteins with which it interacts. For example, at least a portion of the amino acid sequence of a protein which interacts with the huchordin can be ascertained using techniques well known to those of skill in the art, such as via the Edman degradation technique. The amino acid sequence obtained may be used as a guide for the generation of oligonucleotide mixtures that can be used to screen for gene sequences encoding the interacting protein. Screening may be accomplished, for example, by standard hybridization or PCR techniques. Techniques for the generation of oligonucleotide mixtures and the screening are well-known. (Ausubel, supra; and "PCR Protocols: A Guide to Methods and Applications," Innis et al., eds. Academic Press, Inc., NY, 1990).

Additionally, methods may be employed which result directly in the identification of genes which encode proteins which interact with huchordin. These methods include, for example, screening expression libraries, in a manner similar to the well known technique of antibody probing of λgt11 libraries, using labeled huchordin polypeptide or a huchordin fusion protein, e.g., a huchordin polypeptide or domain fused to a marker such as an enzyme, fluorescent dye, a luminescent protein, or to an IgFc domain.

There are also methods which are capable of detecting protein-protein interaction. A method which detects protein interactions in vivo is the two-hybrid system (Chien et al., *Proc. Natl. Acad. Sci. USA*, 88:9578, 1991). A kit for practicing this method is available from Clontech (Palo Alto, Calif.).

Briefly, utilizing such a system, plasmids are constructed that encode two hybrid proteins: one plasmid includes a nucleotide sequence encoding the DNA-binding domain of a transcription activator protein fused to a nucleotide sequence encoding huchordin, a huchordin polypeptide, or a huchordin fusion protein, and the other plasmid includes a nucleotide sequence encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast Saccharomyces cerevisiae that contains a reporter gene (e.g., HBS or LacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system, three-hybrid system or related methodology may be used to screen activation domain libraries for proteins that interact with the "bait" gene product. By way of example, and not by way of limitation, huchordin may be used as the bait gene product. Total genomic or cDNA sequences are fused to the DNA encoding an activation domain. This library and a plasmid encoding a hybrid of bait huchordin gene product fused to the DNA-binding domain are cotransformed into a yeast reporter strain, and the resulting transformants are screened for those that express the reporter gene. For example, a bait huchordin gene sequence, such as huchordin or a domain of huchordin can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait huchordin gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait huchordin gene-GAL4 fusion plasmid into a yeast strain which contains a lacZ gene driven by a promoter which contains GAL4 activation sequence. A cDNA encoded protein, fused to GAL4 transcriptional activation domain, that interacts with bait huchordin gene product will reconstitute an active GAL4 protein and thereby drive expression of the HIS3 gene. Colonies which express HIS3 can then be purified from these strains, and used to produce and isolate the bait huchordin gene-interacting protein using techniques routinely practiced in the art.

Identification of a Huchordin Receptor

A huchordin receptor can be identified as follows. First cells or tissues which bind huchordin are identified. An expression library is prepared using mRNA isolated from huchordin binding cells. The expression library is used to tranfect, eukaryotic cells, e.g., CHO cells. Detectably labelled huchordin is used to identify clones which bind huchordin. These clones are isolated and purified. The expression plasmid is then isolated from the huchordin-binding clones. These expression plasmids will encode putative huchordin receptors.

Identification of Compounds that Modulate the Expression or Activity of Huchordin Isolation of the nucleic acid molecules described above (i.e. those encoding huchordin also facilitates the identification of compounds that can increase or decrease the expression of these molecules in vivo. To discover such compounds, cells that express huchordin are cultured, exposed to a test compound (or a mixture of test compounds), and the level of huchordin expression or activity is compared with the level of expression or activity in cells that are otherwise identical but that have not been exposed to the test compound(s). Many standard quantitative assays of gene expression can be utilized in this aspect of the invention. Examples of these assays are provided below.

In order to identify compounds that modulate expression of huchordin (or homologous genes), the candidate compound(s) can be added at varying concentrations to the culture medium of cells that express huchordin, as described above. These compounds can include small molecules, polypeptides, and nucleic acids. The expression of huchordin is then measured, for example, by Northern blot, PCR analyses or RNAse protection analyses using a nucleic acid molecule of the invention as a probe. The level of expression of the polypeptides of the invention in the presence of the candidate molecule, compared with their level of expression in its absence, will indicate whether or not the candidate molecule alters the expression of huchordin.

Similarly, compounds that modulate the expression of the polypeptides of the invention can be identified by carrying out the assay described above and then performing a Western blot analysis using antibodies that bind huchordin.

Compounds that can be screened in accordance with the invention include, but are not limited to peptides, antibodies and fragments thereof, and other organic compounds (e.g., peptidomimetics).

Such compounds can include, but are not limited to, peptides such as, for example, soluble peptides, including but not limited to members of random peptide libraries; (see, e.g., Lam et al., *Nature* 354:82, 1991; Houghten et al., *Nature* 354:84, 1991), and combinatorial chemistry-derived molecular library made of D- and/or L-configuration amino acids, phosphopeptides (including, but not limited to, members of random or partially degenerate, directed phosphopeptide libraries; see, e.g., Songyang et al., *Cell* 72:767, 1993), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Other compounds that can be screened in accordance with the invention include but are not limited to small organic molecules that affect the expression of the huchordin gene or some other gene involved in a pathway (e.g., signal transduction pathway) involving huchordin (e.g., by interacting with the regulatory region or transcription factors involved in gene expression).

Compounds which Bind Huchordin

Compounds which bind huchordin can be identified using any standard binding assay. The principle of the assays used to identify compounds that bind to huchordin involves preparing a reaction mixture of huchordin and the test compound under conditions and for a time sufficient to allow the two components to interact and bind, thus forming a complex which can be removed and/or detected in the reaction mixture.

The screening assays can be conducted in a variety of ways. For example, one method to conduct such an assay would involve anchoring the huchordin protein, polypeptide, peptide or fusion protein or the test substance onto a solid phase and detecting huchordin/test compound complexes anchored on the solid phase at the end of the reaction. In one embodiment of such a method, huchordin may be anchored onto a solid surface, and the test compound, which is not anchored, may be labeled, either directly or indirectly.

In practice, microtiter plates may conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; for example, using a labeled antibody specific for the previously nonimmobilized component (the antibody, in turn, can be directly labeled or indirectly labeled with a labeled anti-Ig antibody).

Alternatively, a reaction can be conducted in a liquid phase, the reaction products separated from unreacted components, and complexes detected; for example, using an immobilized antibody specific for a huchordin protein, polypeptide, peptide or fusion protein or the test compound to anchor any complexes formed in solution, and a labeled antibody specific for the other component of the possible complex to detect anchored complexes.

Alternatively, cell-based assays can be used to identify compounds that interact with huchordin. To this end, cell lines that express huchordin or cell lines (e.g., COS cells, CHO cells, fibroblasts, etc.) that have been genetically engineered to express huchordin (e.g., by transfection or transduction of huchordin DNA) can be used.

Therapeutic Applications

Huchordin nucleic acid molecules, polypeptides, and huchordin molecules capable of altering huchordin expression, activity, or localization can be used to treat a patient suffering from a disorder associated with aberrant expression or activity huchordin. Such compounds may be used to inhibit fibrosis or angiogenesis.

Diagnostic Applications

The polypeptides of the invention and the antibodies specific for these polypeptides are also useful for identifying those compartments of mammalian cells that contain proteins important to the function of huchordin. Antibodies specific for huchordin can be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

Antibodies specific for huchordin also can be used to detect or monitor huchordin-related diseases. For example, levels of a huchordin protein in a sample can be assayed by any standard technique using these antibodies. For example, huchordin protein expression can be monitored by standard immunological or immunohistochemical procedures (e.g., those described above) using the antibodies described herein. Alternatively, huchordin expression can be assayed by standard Northern blot analysis or can be aided by PCR (see, e.g., Ausubel et al., supra; *PCR Technology: Principles and Applications for DNA Amplification*, ed., H. A. Ehrlich, Stockton Press, N.Y.). If desired or necessary, analysis can be carried out to detect point mutations in the huchordin sequence (for example, using well known nucleic acid mismatch detection techniques). All of the above techniques are enabled by the huchordin sequences described herein.

In addition, the present invention encompasses methods and compositions for the diagnostic evaluation, typing, and prognosis of disorders associated with inappropriate expression or activity of huchordin. For example, the nucleic acid molecules of the invention can be used as diagnostic hybridization probes to detect, for example, inappropriate expression of huchordin or mutations in the huchordin gene. Such methods may be used to classify cells by the level of huchordin expression.

Thus, the invention features a method for diagnosing a disorder associated with aberrant activity of huchordin, the method including obtaining a biological sample from a patient and measuring huchordin activity in the biological sample, wherein increased or decreased huchordin activity in the biological sample compared to a control indicates that the patient suffers from a disorder associated with aberrant activity of huchordin.

High density oligonucleotide probe arrays can be used to detect mutations or polymorphism in the huchordin gene. A tiling array (Cronin et al., *Human Mutation* 7:244, 1996; Kozal et al., *Nature Med.* 2:753, 1996) can be used to location mutations anywhere in the gene. A mutation array (Cronin et al., *Human Mutation* 7:244, 1996) can be used to detect the presence of previously identified mutations.

The present invention further provides for diagnostic kits for the practice of such methods.

Effective Dose

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

EXAMPLE

Described below is the identification, sequencing, and characterization of a human huchordin gene.

A novel open reading frame was identified during genomic sequencing of a human bacterial artificial chromosome. The open reading frame was located approximately 4 kb upstream of the thrombopoietin gene. A genomic fragment within the open reading frame was used to probe a human brain cDNA library (Clontech; Palo Alto, Calif.). A near full-length cDNA clone, lacking only two nucleotides of the initial Met codon, was identified. The identity of the missing nucleotides was confirmed by comparison to the genomic sequence. The cDNA clone encoded a 867 amino acid protein. The cDNA sequence of huchordin is shown in FIGS. 1A–1C (SEQ ID NO:1). The huchordin encoding portion of this cDNA extends from nucleotide 1 to nucleotide 2601 (SEQ ID NO:1). The amino acid sequence of huchordin is also shown in FIGS. 1A–1C (SEQ ID NO:2).

Huchordin is predicted to be a secreted protein having a signal sequence extending from amino acid 1 to amino acid 26. At the amino acid level, huchordin is 53% identical to Xenopus chordin (Sasai et al., Cell 79:779, 1994). FIGS. 2A–2C is an alignment of a portion of the amino acid sequence of huchoridin and a portion of the amino acid sequence of Xenopus chordin (SEQ ID NO:4). Variants of huchordin which are more likely to retain activity do not have alterations at the amino acid positions conserved between huchordin and chordin.

A human Northern blots (Clontech; Palo Alto, Calif.) probed with a full-length huchordin cDNA clone revealed the presence of an approximately 7.5 kb transcript in adult liver and fetal liver, an approximately 2.7 kb transcript in fetal liver, and an approximately 4.4 kb transcript in brain, heart, and pancreas.

As noted above, huchordin has homology to Xenopus chordin, a secreted molecule that functions as a dorsalizing factor in early embryo development. Chordin binds and antagonizes BMP-4, a member of the TGF-beta superfamily.

Huchordin may bind members of the TGF-beta superfamily, e.g., TGF-beta. To the extent that huchordin (or fragments thereof) bind TGF-beta, huchordin can be used to reduce TGF-beta activity, for example, to reduce fibrosis of the kidney, liver, or lung.

The cysteine rich repeats of huchordin are found in thrombospondin-1, thrombospondin-2, and procollagen, protein with anti-angiogenic activity. Thus, huchordin (or fragments thereof which include one or more of the cysteine rich repeats) can be used to inhibit angiogenesis. Such inhibition is useful in limiting tumor growth.

Deposit Statement

E. coli strain fth66 harboring a huchordin cDNA clone was deposited with the American Type Culture Collection 10801 University Boulevard, Manassas, Va. 20110–2209, on Jul. 2, 1997 and given ATCC Accession No. 98481.

This culture has been deposited under conditions that assure that access to the culture will be available during the pendency of the patent application to one determined by the Commissioner of Patents and Trademarks to be entitled thereto under 37 CFR 1.14 and 35 U.S.C. 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposits, and in any case, for a period of at least 30 (thirty) years after the date of deposit or for the enforceable life of any patent which may issue disclosing the culture plus five years after the last request for a sample from the deposit. The depositor acknowledges the duty to replace the deposit should the depository be unable to furnish a sample when requested, due to the condition of the deposit. All restrictions on the availability to the public of the deposit will be irrevocably removed upon the granting of a patent disclosing it.

What is claimed is:

1. An isolated nucleic acid molecule comprising a nucleotide sequence which encodes a polypeptide comprising the amino acid sequence of SEQ ID NO:2.

2. An isolated nucleic acid molecule comprising a nucleotide sequence which encodes a polypeptide comprising the amino acid sequence from amino acid 27 to amino acid 867 of SEQ ID NO:2.

3. An isolated nucleic acid molecule comprising a nucleotide sequence which encodes a polypeptide comprising the amino acid sequence encoded by the DNA insert of the clone deposited with ATCC as Accession Number 98481.

4. An isolated nucleic acid molecule comprising a nucleotide sequence which encodes the mature polypeptide encoded by the DNA insert of the clone deposited with ATCC as Accession Number 98481.

5. An isolated nucleic acid molecule comprising the nucleotide sequence of SEQ ID NO:1 or the complement thereof.

6. An isolated nucleic acid molecule comprising the nucleotide sequence from nucleotide 1 to nucleotide 2601 of SEQ ID NO:1 or the complement thereof.

7. An isolated nucleic acid molecule comprising the nucleotide sequence of the DNA insert of the clone deposited with ATCC as Accession Number 98481, or the complement thereof.

8. An isolated nucleic acid molecule comprising a nucleotide sequence encoding a polypeptide consisting of the amino acid sequence of SEQ ID NO:2, or the complement thereof.

9. An isolated nucleic acid molecule comprising a nucleotide sequence encoding a polypeptide consisting of the amino acid sequence from amino acid 27 to amino acid 867 of SEQ ID NO:2, or the complement thereof.

10. An isolated nucleic acid molecule comprising a nucleotide sequence encoding a polypeptide consisting of the amino acid sequence encoded by the DNA insert of the clone deposited with ATCC as Accession Number 98481, or the complement thereof.

11. An isolated nucleic acid molecule comprising a nucleotide sequence encoding a polypeptide consisting of the amino acid sequence of the mature polypeptide encoded by the DNA insert of the clone deposited with ATCC as Accession Number 98481, or the complement thereof.

12. An isolated nucleic acid molecule consisting of the nucleotide sequence of SEQ ID NO:1 or the complement thereof.

13. An isolated nucleic acid molecule consisting of the nucleotide sequence from nucleotide 1 to nucleotide 2601 of SEQ ID NO:1 or the complement thereof.

14. An isolated nucleic acid molecule consisting of the nucleotide sequence of the DNA insert of the clone deposited with ATCC as Accession Number 98481 or the complement thereof.

15. A vector comprising the nucleic acid molecule of any one of claims 1–4 or 6–14.

16. A host cell which contains the vector of claim 15.

17. A host cell which contains the nucleic acid molecule as in one of claims 1–4, 5–14.

18. The host cell of claim 16 which is a mammalian host cell.

19. The host cell of claim 17 which is a mammalian host cell.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3037 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 1...2601

(xi) SEQUENCE DESCRIPTION: SEQ ID NO:1:

```
ATG CCG AGC CTC CCG GCC CCG CCG GCC CCG CTG CTG CTC CTC GGG CTG         48
Met Pro Ser Leu Pro Ala Pro Pro Ala Pro Leu Leu Leu Leu Gly Leu
 1               5                  10                  15

CTG CTG CTC GGC TCC CGG CCG GCC CGC GGC GCC GGC CCA GAG CCC CCC         96
Leu Leu Leu Gly Ser Arg Pro Ala Arg Gly Ala Gly Pro Glu Pro Pro
             20                  25                  30

GTG CTG CCC ATC CGT TCT GAG AAG GAG CCG CTG CCC GTT CGG GGA GCG        144
Val Leu Pro Ile Arg Ser Glu Lys Glu Pro Leu Pro Val Arg Gly Ala
         35                  40                  45
```

-continued

```
GCA GGC TGC ACC TTC GGC GGG AAG GTC TAT GCC TTG GAC GAG ACG TGG      192
Ala Gly Cys Thr Phe Gly Gly Lys Val Tyr Ala Leu Asp Glu Thr Trp
 50                  55                  60

CAC CCG GAC CTA GGG GAG CCA TTC GGG GTG ATG CGC TGC GTG CTG TGC      240
His Pro Asp Leu Gly Glu Pro Phe Gly Val Met Arg Cys Val Leu Cys
 65                  70                  75                  80

GCC TGC GAG GCG CCT CAG TGG GGT CGC CGT ACC AGG GGC CCT GGC AGG      288
Ala Cys Glu Ala Pro Gln Trp Gly Arg Arg Thr Arg Gly Pro Gly Arg
                 85                  90                  95

GTC AGC TGC AAG AAC ATC AAA CCA GAG TGC CCA ACC CCG GCC TGT GGG      336
Val Ser Cys Lys Asn Ile Lys Pro Glu Cys Pro Thr Pro Ala Cys Gly
            100                 105                 110

CAG CCG CGC CAG CTG CCG GGA CAC TGC TGC CAG ACC TGC CCC CAG GAG      384
Gln Pro Arg Gln Leu Pro Gly His Cys Cys Gln Thr Cys Pro Gln Glu
        115                 120                 125

CGC AGC AGT TCG GAG CGG CAG CCG AGC GGC CTG TCC TTC GAG TAT CCG      432
Arg Ser Ser Ser Glu Arg Gln Pro Ser Gly Leu Ser Phe Glu Tyr Pro
130                 135                 140

CGG GAC CCG GAG CAT CGC AGT TAT AGC GAC CGC GGG GAG CCA GGC GCT      480
Arg Asp Pro Glu His Arg Ser Tyr Ser Asp Arg Gly Glu Pro Gly Ala
145                 150                 155                 160

GAG GAG CGG GCC CGT GGT GAC GGC CAC ACG GAC TTC GTG GCG CTG CTG      528
Glu Glu Arg Ala Arg Gly Asp Gly His Thr Asp Phe Val Ala Leu Leu
                165                 170                 175

ACA GGG CCG AGG TCG CAG GCG GTG GCA CGA GCC CGA GTC TCG CTG CTG      576
Thr Gly Pro Arg Ser Gln Ala Val Ala Arg Ala Arg Val Ser Leu Leu
            180                 185                 190

CGC TCT AGC CTC CGC TTC TCT ATC TCC TAC AGG CGG CTG GAC CGC CCT      624
Arg Ser Ser Leu Arg Phe Ser Ile Ser Tyr Arg Arg Leu Asp Arg Pro
        195                 200                 205

ACC AGG ATC CGC TTC TCA GAC TCC AAT GGC AGT GTC CTG TTT GAG CAC      672
Thr Arg Ile Arg Phe Ser Asp Ser Asn Gly Ser Val Leu Phe Glu His
210                 215                 220

CCT GCA GCC CCC ACC CAA GAT GGC CTG GTC TGT GGG GTG TGG CGG GCA      720
Pro Ala Ala Pro Thr Gln Asp Gly Leu Val Cys Gly Val Trp Arg Ala
225                 230                 235                 240

GTG CCT CGG TTG TCT CTG CGG CTC CTT AGG GCA GAA CAG CTG CAT GTG      768
Val Pro Arg Leu Ser Leu Arg Leu Leu Arg Ala Glu Gln Leu His Val
                245                 250                 255

GCA CTT GTG ACA CTC ACT CAC CCT TCA GGG GAG GTC TGG GGG CCT CTC      816
Ala Leu Val Thr Leu Thr His Pro Ser Gly Glu Val Trp Gly Pro Leu
            260                 265                 270

ATC CGG CAC CGG GCC CTG GCT GCA GAG ACC TTC AGT GCC ATC CTG ACT      864
Ile Arg His Arg Ala Leu Ala Ala Glu Thr Phe Ser Ala Ile Leu Thr
        275                 280                 285

CTA GAA GGC CCC CCA CAG CAG GGC GTA GGG GGC ATC ACC CTG CTC ACT      912
Leu Glu Gly Pro Pro Gln Gln Gly Val Gly Gly Ile Thr Leu Leu Thr
290                 295                 300

CTC AGT GAC ACA GAG GAC TCC TTG CAT TTT TTG CTG CTC TTC CGA GGG      960
Leu Ser Asp Thr Glu Asp Ser Leu His Phe Leu Leu Leu Phe Arg Gly
305                 310                 315                 320

CTG CTG GAA CCC AGG AGT GGG GGA CTA ACC CAG GTT CCC TTG AGG CTC     1008
Leu Leu Glu Pro Arg Ser Gly Gly Leu Thr Gln Val Pro Leu Arg Leu
                325                 330                 335

CAG ATT CTA CAC CAG GGG CAG CTA CTG CGA GAA CTT CAG GCC AAT GTC     1056
Gln Ile Leu His Gln Gly Gln Leu Leu Arg Glu Leu Gln Ala Asn Val
            340                 345                 350

TCA GCC CAG GAA CCA GGC TTT GCT GAG GTG CTG CCC AAC CTG ACA GTC     1104
Ser Ala Gln Glu Pro Gly Phe Ala Glu Val Leu Pro Asn Leu Thr Val
        355                 360                 365
```

```
CAG GAG ATG GAC TGG CTG GTG CTG GGG GAG CTG CAG ATG GCC CTG GAG         1152
Gln Glu Met Asp Trp Leu Val Leu Gly Glu Leu Gln Met Ala Leu Glu
        370                 375                 380

TGG GCA GGC AGG CCA GGG CTG CGC ATC AGT GGA CAC ATT GCT GCC AGG         1200
Trp Ala Gly Arg Pro Gly Leu Arg Ile Ser Gly His Ile Ala Ala Arg
385                 390                 395                 400

AAG AGC TGC GAC GTC CTG CAA AGT GTC CTT TGT GGG GCT GAT GCC CTG         1248
Lys Ser Cys Asp Val Leu Gln Ser Val Leu Cys Gly Ala Asp Ala Leu
                405                 410                 415

ATC CCA GTC CAG ACG GGT GCT GCC GGC TCA GCC AGC CTC ACG CTG CTA         1296
Ile Pro Val Gln Thr Gly Ala Ala Gly Ser Ala Ser Leu Thr Leu Leu
            420                 425                 430

GGA AAT GGC TCC CTG ATC TAT CAG GTG CAA GTG GTA GGG ACA AGC AGT         1344
Gly Asn Gly Ser Leu Ile Tyr Gln Val Gln Val Val Gly Thr Ser Ser
                435                 440                 445

GAG GTG GTG GCC ATG ACA CTG GAG ACC AAG CCT CAG CGG AGG GAT CAG         1392
Glu Val Val Ala Met Thr Leu Glu Thr Lys Pro Gln Arg Arg Asp Gln
        450                 455                 460

CGC ACT GTC CTG TGC CAC ATG GCT GGA CTC CAG CCA GGA GGA CAC ACG         1440
Arg Thr Val Leu Cys His Met Ala Gly Leu Gln Pro Gly Gly His Thr
465                 470                 475                 480

GCC GTG GGT ATC TGC CCT GGG CTG GGT GCC CGA GGG GCT CAT ATG CTG         1488
Ala Val Gly Ile Cys Pro Gly Leu Gly Ala Arg Gly Ala His Met Leu
                485                 490                 495

CTG CAG AAT GAG CTC TTC CTG AAC GTG GGC ACC AAG GAC TTC CCA GAC         1536
Leu Gln Asn Glu Leu Phe Leu Asn Val Gly Thr Lys Asp Phe Pro Asp
            500                 505                 510

GGA GAG CTT CGG GGG CAC GTG GCT GCC CTG CCC TAC TGT GGG CAT AGC         1584
Gly Glu Leu Arg Gly His Val Ala Ala Leu Pro Tyr Cys Gly His Ser
                515                 520                 525

GCC CGC CAT GAC ACG CTG TCC GTG CCC CTA GCA GGA GCC CTG GTG CTA         1632
Ala Arg His Asp Thr Leu Ser Val Pro Leu Ala Gly Ala Leu Val Leu
530                 535                 540

CCC CCT GTG AAG AGC CAA GCA GCA GGG CAC GCC TGG CTT TCC TTG GAT         1680
Pro Pro Val Lys Ser Gln Ala Ala Gly His Ala Trp Leu Ser Leu Asp
545                 550                 555                 560

ACC CAC TGT CAC CTG CAC TAT GAA GTG CTG CTG GCT GGG CTT GGT GGC         1728
Thr His Cys His Leu His Tyr Glu Val Leu Leu Ala Gly Leu Gly Gly
                565                 570                 575

TCA GAA CAA GGC ACT GTC ACT GCC CAC CTC CTT GGG CCT CCT GGA ACG         1776
Ser Glu Gln Gly Thr Val Thr Ala His Leu Leu Gly Pro Pro Gly Thr
            580                 585                 590

CCA GGG CCT CGG CGG CTG CTG AAG GGA TTC TAT GGC TCA GAG GCC CAG         1824
Pro Gly Pro Arg Arg Leu Leu Lys Gly Phe Tyr Gly Ser Glu Ala Gln
        595                 600                 605

GGT GTG GTG AAG GAC CTG GAG CCG GAA CTG CTG CGG CAC CTG GCA AAA         1872
Gly Val Val Lys Asp Leu Glu Pro Glu Leu Leu Arg His Leu Ala Lys
610                 615                 620

GGC ATG GCC TCC CTG ATG ATC ACC ACC AAG GGT AGC CCC AGA GGG GAG         1920
Gly Met Ala Ser Leu Met Ile Thr Thr Lys Gly Ser Pro Arg Gly Glu
625                 630                 635                 640

CTC CGA GGG CAG AGA CGA ACG GTG ATC TGT GAC CCG GTG GTG TGC CCA         1968
Leu Arg Gly Gln Arg Arg Thr Val Ile Cys Asp Pro Val Val Cys Pro
                645                 650                 655

CCG CCC AGC TGC CCA CAC CCG GTG CAG GCT CCC GAC CAG TGC TGC CCT         2016
Pro Pro Ser Cys Pro His Pro Val Gln Ala Pro Asp Gln Cys Cys Pro
            660                 665                 670

GTT TGC CCT GAG AAA CAA GAT GTC AGA GAC TTG CCA GGG CTG CCA AGG         2064
Val Cys Pro Glu Lys Gln Asp Val Arg Asp Leu Pro Gly Leu Pro Arg
        675                 680                 685
```

```
AGC CGG GAC CCA GGA GAG GGC TGC TAT TTT GAT GGT GAC CGG AGC TGG     2112
Ser Arg Asp Pro Gly Glu Gly Cys Tyr Phe Asp Gly Asp Arg Ser Trp
    690                 695                 700

CGG GCA GCG GGT ACG CGG TGG CAC CCC GTT GTG CCC CCC TTT GGC TTA     2160
Arg Ala Ala Gly Thr Arg Trp His Pro Val Val Pro Pro Phe Gly Leu
705                 710                 715                 720

ATT AAG TGT GCT GTC TGC ACC TGC AAG GGG GGC ACT GGA GAG GTG CAC     2208
Ile Lys Cys Ala Val Cys Thr Cys Lys Gly Gly Thr Gly Glu Val His
                725                 730                 735

TGT GAG AAG GTG CAG TGT CCC CGG CTG GCC TGT GCC CAG CCT GTG CGT     2256
Cys Glu Lys Val Gln Cys Pro Arg Leu Ala Cys Ala Gln Pro Val Arg
            740                 745                 750

GTC AAC CCC ACC GAC TGC TGC AAA CAG TGT CCA GTG GGG TCG GGG GCC     2304
Val Asn Pro Thr Asp Cys Cys Lys Gln Cys Pro Val Gly Ser Gly Ala
                755                 760                 765

CAC CCC CAG CTG GGG GAC CCC ATG CAG GCT GAT GGG CCC CGG GGC TGC     2352
His Pro Gln Leu Gly Asp Pro Met Gln Ala Asp Gly Pro Arg Gly Cys
            770                 775                 780

CGT TTT GCT GGG CAG TGG TTC CCA GAG AGT CAG AGC TGG CAC CCC TCA     2400
Arg Phe Ala Gly Gln Trp Phe Pro Glu Ser Gln Ser Trp His Pro Ser
785                 790                 795                 800

GTG CCC CCT TTT GGA GAG ATG AGC TGT ATC ACC TGC AGA TGT GGG GCA     2448
Val Pro Pro Phe Gly Glu Met Ser Cys Ile Thr Cys Arg Cys Gly Ala
                805                 810                 815

GGG GTG CCT CAC TGT GAG CGG GAT GAC TGT TCA CTG CCA CTG TCC TGT     2496
Gly Val Pro His Cys Glu Arg Asp Asp Cys Ser Leu Pro Leu Ser Cys
            820                 825                 830

GGC TCG GGG AAG GAG AGT CGA TGC TGT TCC CGC TGC ACG GCC CAC CGG     2544
Gly Ser Gly Lys Glu Ser Arg Cys Cys Ser Arg Cys Thr Ala His Arg
835                 840                 845

CGG CCA GCC CCA GAG ACC AGA ACT GAT CCA GAG CTG GAG AAA GAA GCC     2592
Arg Pro Ala Pro Glu Thr Arg Thr Asp Pro Glu Leu Glu Lys Glu Ala
                850                 855                 860

GAA GGC TCT TAGGGAGCAG CCAGAGGGCC AAGTGACCAA GAGGATGGGG CCTGAGCTG   2650
Glu Gly Ser
865

GGGAAGGGGT GGCATCGAGG ACCTTCTTGC ATTCTCCTGT GGGAAGCCCA GTGCCTTTGC   2710

TCCTCTGTCC TGCCTCTACT CCCACCCCCA CTACCTTTGG GAACCACAGC TCCACAAGGG   2770

GGAGAGGCAG CTGGGCCAGA CCGAGGTCAC AGCCACTCCA AGTCCTGCCC TGCCACCCTC   2830

GGCCTCTGTC CTTGGAAGCC CCACCCCTTT CCTCCTGTAC ATAATGTCAC TGGCTTGTTG   2890

GGATTTTTAA TTTATCTTCA CTCAGCACCA AGGGCCCCCG ACACTCCACT CCTGCTGCCC   2950

CTGAGCTGAG CAGAGTCATT ATTGGAGAGT TTTGTATTTA TTAAAACATT TCTTTTTCAG   3010

TCAAAAAAAA AAAAAAGGG CGGCCGC                                       3037

(2) INFORMATION FOR SEQ ID NO:2:

(i) SEQUENCE CHARACTERISTICS:
        (A) LENGTH: 867 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

Met Pro Ser Leu Pro Ala Pro Pro Ala Pro Leu Leu Leu Leu Gly Leu
 1               5                  10                  15
```

-continued

Leu Leu Leu Gly Ser Arg Pro Ala Arg Gly Ala Gly Pro Glu Pro Pro
            20                  25                  30

Val Leu Pro Ile Arg Ser Glu Lys Glu Pro Leu Pro Val Arg Gly Ala
        35                  40                  45

Ala Gly Cys Thr Phe Gly Gly Lys Val Tyr Ala Leu Asp Glu Thr Trp
    50                  55                  60

His Pro Asp Leu Gly Glu Pro Phe Gly Val Met Arg Cys Val Leu Cys
65                  70                  75                  80

Ala Cys Glu Ala Pro Gln Trp Gly Arg Arg Thr Arg Gly Pro Gly Arg
                85                  90                  95

Val Ser Cys Lys Asn Ile Lys Pro Glu Cys Pro Thr Pro Ala Cys Gly
            100                 105                 110

Gln Pro Arg Gln Leu Pro Gly His Cys Cys Gln Thr Cys Pro Gln Glu
        115                 120                 125

Arg Ser Ser Ser Glu Arg Gln Pro Ser Gly Leu Ser Phe Glu Tyr Pro
    130                 135                 140

Arg Asp Pro Glu His Arg Ser Tyr Ser Asp Arg Gly Glu Pro Gly Ala
145                 150                 155                 160

Glu Glu Arg Ala Arg Gly Asp Gly His Thr Asp Phe Val Ala Leu Leu
                165                 170                 175

Thr Gly Pro Arg Ser Gln Ala Val Ala Arg Ala Arg Val Ser Leu Leu
            180                 185                 190

Arg Ser Ser Leu Arg Phe Ser Ile Ser Tyr Arg Arg Leu Asp Arg Pro
        195                 200                 205

Thr Arg Ile Arg Phe Ser Asp Ser Asn Gly Ser Val Leu Phe Glu His
    210                 215                 220

Pro Ala Ala Pro Thr Gln Asp Gly Leu Val Cys Gly Val Trp Arg Ala
225                 230                 235                 240

Val Pro Arg Leu Ser Leu Arg Leu Leu Arg Ala Glu Gln Leu His Val
                245                 250                 255

Ala Leu Val Thr Leu Thr His Pro Ser Gly Glu Val Trp Gly Pro Leu
            260                 265                 270

Ile Arg His Arg Ala Leu Ala Ala Glu Thr Phe Ser Ala Ile Leu Thr
        275                 280                 285

Leu Glu Gly Pro Pro Gln Gln Gly Val Gly Gly Ile Thr Leu Leu Thr
    290                 295                 300

Leu Ser Asp Thr Glu Asp Ser Leu His Phe Leu Leu Leu Phe Arg Gly
305                 310                 315                 320

Leu Leu Glu Pro Arg Ser Gly Gly Leu Thr Gln Val Pro Leu Arg Leu
                325                 330                 335

Gln Ile Leu His Gln Gly Gln Leu Leu Arg Glu Leu Gln Ala Asn Val
            340                 345                 350

Ser Ala Gln Glu Pro Gly Phe Ala Glu Val Leu Pro Asn Leu Thr Val
        355                 360                 365

Gln Glu Met Asp Trp Leu Val Leu Gly Glu Leu Gln Met Ala Leu Glu
    370                 375                 380

Trp Ala Gly Arg Pro Gly Leu Arg Ile Ser Gly His Ile Ala Ala Arg
385                 390                 395                 400

Lys Ser Cys Asp Val Leu Gln Ser Val Leu Cys Gly Ala Asp Ala Leu
                405                 410                 415

Ile Pro Val Gln Thr Gly Ala Ala Gly Ser Ala Ser Leu Thr Leu Leu
            420                 425                 430

Gly Asn Gly Ser Leu Ile Tyr Gln Val Gln Val Val Gly Thr Ser Ser
        435                 440                 445

-continued

Glu Val Val Ala Met Thr Leu Glu Thr Lys Pro Gln Arg Arg Asp Gln
450                     455                 460

Arg Thr Val Leu Cys His Met Ala Gly Leu Gln Pro Gly His Thr
465                 470                 475                 480

Ala Val Gly Ile Cys Pro Gly Leu Gly Ala Arg Gly Ala His Met Leu
            485                 490                 495

Leu Gln Asn Glu Leu Phe Leu Asn Val Gly Thr Lys Asp Phe Pro Asp
            500                 505                 510

Gly Glu Leu Arg Gly His Val Ala Ala Leu Pro Tyr Cys Gly His Ser
            515                 520             525

Ala Arg His Asp Thr Leu Ser Val Pro Leu Ala Gly Ala Leu Val Leu
530                 535                 540

Pro Pro Val Lys Ser Gln Ala Ala Gly His Ala Trp Leu Ser Leu Asp
545                 550                 555                 560

Thr His Cys His Leu His Tyr Glu Val Leu Leu Ala Gly Leu Gly Gly
                565                 570                 575

Ser Glu Gln Gly Thr Val Thr Ala His Leu Leu Gly Pro Pro Gly Thr
            580                 585                 590

Pro Gly Pro Arg Arg Leu Leu Lys Gly Phe Tyr Gly Ser Glu Ala Gln
        595                 600                 605

Gly Val Val Lys Asp Leu Glu Pro Glu Leu Leu Arg His Leu Ala Lys
        610                 615                 620

Gly Met Ala Ser Leu Met Ile Thr Thr Lys Gly Ser Pro Arg Gly Glu
625                 630                 635                 640

Leu Arg Gly Gln Arg Arg Thr Val Ile Cys Asp Pro Val Val Cys Pro
                645                 650                 655

Pro Pro Ser Cys Pro His Pro Val Gln Ala Pro Asp Gln Cys Cys Pro
            660                 665                 670

Val Cys Pro Glu Lys Gln Asp Val Arg Asp Leu Pro Gly Leu Pro Arg
        675                 680                 685

Ser Arg Asp Pro Gly Glu Gly Cys Tyr Phe Asp Gly Asp Arg Ser Trp
    690                 695                 700

Arg Ala Ala Gly Thr Arg Trp His Pro Val Val Pro Pro Phe Gly Leu
705                 710                 715                 720

Ile Lys Cys Ala Val Cys Thr Cys Lys Gly Gly Thr Gly Glu Val His
                725                 730                 735

Cys Glu Lys Val Gln Cys Pro Arg Leu Ala Cys Ala Gln Pro Val Arg
            740                 745                 750

Val Asn Pro Thr Asp Cys Cys Lys Gln Cys Pro Val Gly Ser Gly Ala
            755                 760                 765

His Pro Gln Leu Gly Asp Pro Met Gln Ala Asp Gly Pro Arg Gly Cys
        770                 775                 780

Arg Phe Ala Gly Gln Trp Phe Pro Glu Ser Gln Ser Trp His Pro Ser
785                 790                 795                 800

Val Pro Pro Phe Gly Glu Met Ser Cys Ile Thr Cys Arg Cys Gly Ala
                805                 810                 815

Gly Val Pro His Cys Glu Arg Asp Asp Cys Ser Leu Pro Leu Ser Cys
            820                 825                 830

Gly Ser Gly Lys Glu Ser Arg Cys Cys Ser Arg Cys Thr Ala His Arg
        835                 840                 845

Arg Pro Ala Pro Glu Thr Arg Thr Asp Pro Glu Leu Glu Lys Glu Ala
        850                 855                 860

Glu Gly Ser
865

(2) INFORMATION FOR SEQ ID NO:3:

(i) SEQUENCE CHARACTERISTICS:
        (A) LENGTH: 855 amino acids
        (B) TYPE: amino acid
        (D) TOPOLOGY: linear (ii) MOLECULE TYPE: protein (xi) SEQUENCE DESCRIPTION: SEQ ID NO:3:

```
Ala Pro Pro Ala Pro Leu Leu Leu Gly Leu Leu Leu Gly Ser
  1               5                  10                  15

Arg Pro Ala Arg Gly Ala Gly Pro Glu Pro Val Leu Pro Ile Arg
             20                  25                  30

Ser Glu Lys Glu Pro Leu Pro Val Arg Gly Ala Ala Gly Cys Thr Phe
             35                  40                  45

Gly Gly Lys Val Tyr Ala Leu Asp Glu Thr Trp His Pro Asp Leu Gly
 50                  55                  60

Glu Pro Phe Gly Val Met Arg Cys Val Leu Cys Ala Cys Glu Ala Pro
 65                  70                  75                  80

Gln Trp Gly Arg Arg Thr Arg Gly Pro Gly Arg Val Ser Cys Lys Asn
             85                  90                  95

Ile Lys Pro Glu Cys Pro Thr Pro Ala Cys Gly Gln Pro Arg Gln Leu
            100                 105                 110

Pro Gly His Cys Cys Gln Thr Cys Pro Gln Glu Arg Ser Ser Ser Glu
            115                 120                 125

Arg Gln Pro Ser Gly Leu Ser Phe Glu Tyr Pro Arg Asp Pro Glu His
130                 135                 140

Arg Ser Tyr Ser Asp Arg Gly Glu Pro Gly Ala Glu Glu Arg Ala Arg
145                 150                 155                 160

Gly Asp Gly His Thr Asp Phe Val Ala Leu Leu Thr Gly Pro Arg Ser
                165                 170                 175

Gln Ala Val Ala Arg Ala Arg Val Ser Leu Leu Arg Ser Ser Leu Arg
            180                 185                 190

Phe Ser Ile Ser Tyr Arg Arg Leu Asp Arg Pro Thr Arg Ile Arg Phe
            195                 200                 205

Ser Asp Ser Asn Gly Ser Val Leu Phe Glu His Pro Ala Ala Pro Thr
210                 215                 220

Gln Asp Gly Leu Val Cys Gly Val Trp Arg Ala Val Pro Arg Leu Ser
225                 230                 235                 240

Leu Arg Leu Leu Arg Ala Glu Gln Leu His Val Ala Leu Val Thr Leu
                245                 250                 255

Thr His Pro Ser Gly Glu Val Trp Gly Pro Leu Ile Arg His Arg Ala
            260                 265                 270

Leu Ala Ala Glu Thr Phe Ser Ala Ile Leu Thr Leu Glu Gly Pro Pro
            275                 280                 285

Gln Gln Gly Val Gly Gly Ile Thr Leu Leu Thr Leu Ser Asp Thr Glu
290                 295                 300

Asp Ser Leu His Phe Leu Leu Leu Phe Arg Gly Leu Leu Glu Pro Arg
305                 310                 315                 320

Ser Gly Gly Leu Thr Gln Val Pro Leu Arg Leu Gln Ile Leu His Gln
                325                 330                 335

Gly Gln Leu Leu Arg Glu Leu Gln Ala Asn Val Ser Ala Gln Glu Pro
            340                 345                 350
```

```
Gly Phe Ala Glu Val Leu Pro Asn Leu Thr Val Gln Glu Met Asp Trp
            355                 360                 365

Leu Val Leu Gly Glu Leu Gln Met Ala Leu Glu Trp Ala Gly Arg Pro
            370                 375                 380

Gly Leu Arg Ile Ser Gly His Ile Ala Ala Arg Lys Ser Cys Asp Val
385                 390                 395                 400

Leu Gln Ser Val Leu Cys Gly Ala Asp Ala Leu Ile Pro Val Gln Thr
                405                 410                 415

Gly Ala Ala Gly Ser Ala Ser Leu Thr Leu Leu Gly Asn Gly Ser Leu
            420                 425                 430

Ile Tyr Gln Val Gln Val Val Gly Thr Ser Ser Glu Val Val Ala Met
            435                 440                 445

Thr Leu Glu Thr Lys Pro Gln Arg Arg Asp Gln Arg Thr Val Leu Cys
            450                 455                 460

His Met Ala Gly Leu Gln Pro Gly Gly His Thr Ala Val Gly Ile Cys
465                 470                 475                 480

Pro Gly Leu Gly Ala Arg Gly Ala His Met Leu Leu Gln Asn Glu Leu
                485                 490                 495

Phe Leu Asn Val Gly Thr Lys Asp Phe Pro Asp Gly Glu Leu Arg Gly
            500                 505                 510

His Val Ala Ala Leu Pro Tyr Cys Gly His Ser Ala Arg His Asp Thr
            515                 520                 525

Leu Ser Val Pro Leu Ala Gly Ala Leu Val Leu Pro Pro Val Lys Ser
            530                 535                 540

Gln Ala Ala Gly His Ala Trp Leu Ser Leu Asp Thr His Cys His Leu
545                 550                 555                 560

His Tyr Glu Val Leu Leu Val Gly Leu Gly Gly Ser Glu Gln Gly Thr
                565                 570                 575

Val Thr Ala His Leu Leu Gly Pro Pro Gly Thr Pro Gly Pro Arg Arg
            580                 585                 590

Leu Leu Lys Gly Phe Tyr Gly Ser Glu Ala Gln Gly Val Val Lys Asp
            595                 600                 605

Leu Glu Pro Glu Leu Leu Arg His Leu Ala Lys Gly Met Ala Ser Leu
            610                 615                 620

Met Ile Thr Thr Lys Gly Ser Pro Arg Gly Glu Leu Arg Gly Gln Arg
625                 630                 635                 640

Arg Thr Val Ile Cys Asp Pro Val Val Cys Pro Pro Ser Cys Pro
                645                 650                 655

His Pro Val Gln Ala Pro Asp Gln Cys Cys Pro Val Cys Pro Glu Lys
            660                 665                 670

Gln Asp Val Arg Asp Leu Pro Gly Leu Pro Arg Ser Arg Asp Pro Gly
            675                 680                 685

Glu Gly Cys Tyr Phe Asp Gly Asp Arg Ser Trp Arg Ala Ala Gly Thr
            690                 695                 700

Arg Trp His Pro Val Val Pro Pro Phe Gly Leu Ile Lys Cys Ala Val
705                 710                 715                 720

Cys Thr Cys Lys Gly Gly Thr Gly Glu Val His Cys Glu Lys Val Gln
                725                 730                 735

Cys Pro Arg Leu Ala Cys Ala Gln Pro Val Arg Val Asn Pro Thr Asp
            740                 745                 750

Cys Cys Lys Gln Cys Pro Val Gly Ser Gly Ala His Pro Gln Leu Gly
            755                 760                 765
```

-continued

```
Asp Pro Met Gln Ala Asp Gly Pro Arg Gly Cys Arg Phe Ala Gly Gln
770                 775                 780
Trp Phe Pro Glu Ser Gln Ser Trp His Pro Ser Val Pro Pro Phe Gly
785                 790                 795                 800
Glu Met Ser Cys Ile Thr Cys Arg Cys Gly Ala Gly Val Pro His Cys
                805                 810                 815
Glu Arg Asp Asp Cys Ser Leu Pro Leu Ser Cys Gly Ser Gly Lys Glu
                820                 825                 830
Ser Arg Cys Cys Ser Arg Cys Thr Ala His Arg Arg Pro Ala Pro Glu
                835                 840                 845
Thr Arg Thr Asp Pro Glu Leu
850                 855
```

(2) INFORMATION FOR SEQ ID NO:4:

(i) SEQUENCE CHARACTERISTICS:
        (A) LENGTH: 940 amino acids
        (B) TYPE: amino acid
        (D) TOPOLOGY: linear (ii) MOLECULE TYPE: protein (xi) SEQUENCE DESCRIPTION: SEQ ID NO:4:

```
Gln Cys Pro Pro Ile Leu Leu Val Trp Thr Leu Trp Ile Met Ala Val
1               5                   10                  15
Asp Cys Ser Arg Pro Lys Val Phe Leu Pro Ile Gln Pro Glu Gln Glu
                20                  25                  30
Pro Leu Gln Ser Lys Thr Pro Ala Gly Cys Thr Phe Gly Gly Lys Phe
            35                  40                  45
Tyr Ser Leu Glu Asp Ser Trp His Pro Asp Leu Gly Glu Pro Phe Gly
50                  55                  60
Val Met His Cys Val Leu Cys Tyr Cys Glu Pro Gln Arg Ser Arg Arg
65                  70                  75                  80
Gly Lys Pro Ser Gly Lys Val Ser Cys Lys Asn Ile Lys His Asp Cys
                85                  90                  95
Pro Ser Pro Ser Cys Ala Asn Pro Ile Leu Leu Pro Leu His Cys Cys
                100                 105                 110
Lys Thr Cys Pro Lys Ala Pro Pro Pro Ile Lys Lys Ser Asp Phe
            115                 120                 125
Val Phe Asp Gly Phe Glu Tyr Phe Gln Glu Lys Asp Asp Asp Leu Tyr
130                 135                 140
Asn Asp Arg Ser Tyr Leu Ser Ser Asp Val Ala Val Glu Glu Ser
145                 150                 155                 160
Arg Ser Glu Tyr Val Ala Leu Leu Thr Ala Pro Ser His Val Trp Pro
                165                 170                 175
Pro Val Thr Ser Gly Val Ala Lys Ala Arg Phe Asn Leu Gln Arg Ser
                180                 185                 190
Asn Leu Leu Phe Ser Ile Thr Tyr Lys Trp Ile Asp Arg Leu Ser Arg
            195                 200                 205
Ile Arg Phe Ser Asp Leu Asp Gly Ser Val Leu Phe Glu His Pro Val
210                 215                 220
His Arg Met Gly Ser Pro Arg Asp Asp Thr Ile Cys Gly Ile Trp Arg
225                 230                 235                 240
Ser Leu Asn Arg Ser Thr Leu Arg Leu Arg Met Gly His Ile Leu
                245                 250                 255
Val Ser Leu Val Thr Thr Thr Leu Ser Glu Pro Glu Ile Ser Gly Lys
                260                 265                 270
```

```
Ile Val Lys His Lys Ala Leu Phe Ser Glu Ser Phe Ser Ala Leu Leu
        275                 280                 285

Thr Pro Glu Asp Ser Asp Glu Thr Gly Gly Gly Leu Ala Met Leu
        290                 295                 300

Thr Leu Ser Asp Val Asp Asp Asn Leu His Phe Ile Leu Met Leu Arg
305                 310                 315                 320

Gly Leu Ser Gly Glu Glu Gly Asp Gln Ile Pro Ile Leu Val Gln Ile
                325                 330                 335

Ser His Gln Asn His Val Ile Arg Glu Leu Tyr Ala Asn Ile Ser Ala
                340                 345                 350

Gln Glu Gln Asp Phe Ala Glu Val Leu Pro Asp Leu Ser Ser Arg Glu
                355                 360                 365

Met Leu Trp Leu Ala Gln Gly Gln Leu Glu Ile Ser Val Gln Thr Glu
        370                 375                 380

Gly Arg Arg Pro Gln Ser Met Ser Gly Ile Ile Thr Val Arg Lys Ser
385                 390                 395                 400

Cys Asp Thr Leu Gln Ser Val Leu Ser Gly Gly Asp Ala Leu Asn Pro
                405                 410                 415

Thr Lys Thr Gly Ala Val Gly Ser Ala Ser Ile Thr Leu His Glu Asn
                420                 425                 430

Gly Thr Leu Glu Tyr Gln Ile Gln Ile Ala Gly Thr Met Ser Thr Val
        435                 440                 445

Thr Ala Val Thr Leu Glu Thr Lys Pro Arg Arg Lys Thr Lys Arg Asn
450                 455                 460

Ile Leu His Asp Met Ser Lys Asp Tyr His Asp Gly Arg Val Trp Gly
465                 470                 475                 480

Tyr Trp Ile Asp Ala Asn Ala Arg Asp Leu His Met Leu Leu Gln Ser
                485                 490                 495

Glu Leu Phe Leu Asn Val Ala Thr Lys Asp Phe Gln Glu Gly Glu Leu
                500                 505                 510

Arg Gly Gln Ile Thr Pro Leu Leu Tyr Ser Gly Leu Trp Ala Arg Tyr
        515                 520                 525

Glu Lys Leu Pro Val Pro Leu Ala Gly Gln Phe Val Ser Pro Pro Ile
        530                 535                 540

Arg Thr Gly Ser Ala Gly His Ala Trp Val Ser Leu Asp Glu His Cys
545                 550                 555                 560

His Leu His Tyr Gln Ile Val Val Thr Gly Leu Gly Lys Ala Glu Asp
                565                 570                 575

Ala Ala Leu Asn Ala His Leu His Gly Phe Ala Glu Leu Gly Glu Val
                580                 585                 590

Gly Glu Ser Ser Pro Gly His Lys Arg Leu Leu Lys Gly Phe Tyr Gly
        595                 600                 605

Ser Glu Ala Gln Gly Ser Val Lys Asp Leu Asp Leu Glu Leu Leu Gly
        610                 615                 620

His Leu Ser Arg Gly Thr Ala Phe Ile Gln Val Ser Thr Lys Leu Asn
625                 630                 635                 640

Pro Arg Gly Glu Ile Arg Gly Gln Ile His Ile Pro Asn Ser Cys Glu
                645                 650                 655

Ser Gly Gly Val Ser Leu Thr Pro Glu Glu Pro Glu Tyr Glu Tyr Glu
                660                 665                 670

Ile Tyr Glu Glu Gly Arg Gln Arg Asp Pro Asp Asp Leu Arg Lys Asp
        675                 680                 685
```

```
                                        -continued
Pro Arg Ala Cys Ser Phe Glu Gly Gln Leu Arg Ala His Gly Ser Arg
    690                 695                 700
Trp Ala Pro Asp Tyr Asp Arg Lys Cys Ser Val Cys Ser Cys Gln Lys
705                 710                 715                 720
Arg Thr Val Ile Cys Asp Pro Ile Val Cys Pro Pro Leu Asn Cys Ser
                725                 730                 735
Gln Pro Val His Leu Pro Asp Gln Cys Cys Pro Val Cys Glu Glu Lys
            740                 745                 750
Lys Glu Met Arg Glu Val Lys Lys Pro Glu Arg Ala Arg Thr Ser Glu
        755                 760                 765
Gly Cys Phe Asp Gly Asp Arg Ser Trp Lys Ala Ala Gly Thr Arg
    770                 775                 780
Trp His Pro Phe Val Pro Pro Phe Gly Leu Ile Lys Cys Ala Ile Cys
785                 790                 795                 800
Thr Cys Lys Gly Ser Thr Gly Glu Val His Cys Glu Lys Val Thr Cys
                805                 810                 815
Pro Lys Leu Ser Cys Thr Asn Pro Ile Arg Ala Asn Pro Ser Asp Cys
                820                 825                 830
Cys Lys Gln Cys Pro Val Glu Glu Arg Ser Pro Met Glu Leu Ala Asp
        835                 840                 845
Ser Met Gln Ser Asp Gly Ala Gly Ser Cys Arg Phe Gly Arg His Trp
    850                 855                 860
Tyr Pro Asn His Glu Arg Trp His Pro Thr Val Pro Pro Phe Gly Glu
865                 870                 875                 880
Met Lys Cys Val Thr Cys Thr Cys Ala Glu Gly Ile Thr Gln Cys Arg
                885                 890                 895
Arg Gln Glu Cys Thr Gly Thr Thr Cys Gly Thr Gly Ser Lys Arg Asp
            900                 905                 910
Arg Cys Cys Thr Lys Cys Lys Asp Ala Asn Gln Asp Glu Asp Glu Lys
        915                 920                 925
Val Lys Ser Asp Glu Thr Arg Thr Pro Trp Ser Phe
    930                 935                 940
```